(12) United States Patent
Looi et al.

(10) Patent No.: US 8,623,066 B2
(45) Date of Patent: Jan. 7, 2014

(54) CELL SEEDED EXPANDABLE BODY

(75) Inventors: Kareen Looi, Sunnyvale, CA (US);
Gary K. Owens, Earlysville, VA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 1348 days.

(21) Appl. No.: 11/963,624

(22) Filed: Dec. 21, 2007

(65) Prior Publication Data

US 2008/0138378 A1 Jun. 12, 2008

Related U.S. Application Data

(63) Continuation of application No. 10/913,304, filed on Aug. 6, 2004, now abandoned, and a continuation-in-part of application No. PCT/US03/21754, filed on Jul. 11, 2003, and a continuation-in-part of application No. PCT/US03/21611, filed on Jul. 11, 2003.

(60) Provisional application No. 60/494,045, filed on Aug. 7, 2003, provisional application No. 60/395,180, filed on Jul. 11, 2002, provisional application No. 60/421,404, filed on Oct. 24, 2002, provisional application No. 60/421,350, filed on Oct. 24, 2002, provisional application No. 60/428,803, filed on Nov. 25, 2002.

(51) Int. Cl.
*A61F 2/06* (2013.01)

(52) U.S. Cl.
USPC ...................................................... 623/1.15

(58) Field of Classification Search
USPC ........... 623/1.15–1.22, 1.36, 1.39, 1.41, 1.13, 623/1.14
See application file for complete search history.

(56) References Cited

U.S. PATENT DOCUMENTS

| 4,776,337 | A | | 10/1988 | Palmaz |
| 4,787,899 | A | | 11/1988 | Lazarus |
| 4,856,516 | A | | 8/1989 | Hillstead |
| 5,397,355 | A | * | 3/1995 | Marin et al. ................... 623/1.2 |
| 5,514,154 | A | | 5/1996 | Lau et al. |
| 5,591,197 | A | | 1/1997 | Orth et al. |
| 5,593,434 | A | | 1/1997 | Williams |
| 5,605,696 | A | | 2/1997 | Eury et al. |
| 5,681,346 | A | | 10/1997 | Orth et al. |
| 5,800,526 | A | | 9/1998 | Anderson et al. |
| 5,824,039 | A | | 10/1998 | Piplani et al. |

(Continued)

FOREIGN PATENT DOCUMENTS

WO    WO02/074925    9/2002

OTHER PUBLICATIONS

Creel et al., "Arterial Paclitaxel Distribution and Deposition" Circulation Research (2000) 86 :879-884.

(Continued)

*Primary Examiner* — Melanie Tyson

(57) ABSTRACT

Devices, systems and methods for treating medical conditions using cell therapy via body lumens. Localized delivery is achieved with the use of a stent-like expandable body seeded with cells. The expandable body is expanded to contact at least a portion of the inner walls of the body lumen and the cells, cellular products and/or other therapeutic agents are delivered to the surrounding tissue. The therapeutic benefit provided is dependent on the type of cells used and the features of the expandable body.

29 Claims, 18 Drawing Sheets

(56) References Cited

U.S. PATENT DOCUMENTS

| | | | |
|---|---|---|---|
| 6,113,621 A | 9/2000 | Wiktor | |
| 6,197,013 B1 | 3/2001 | Reed et al. | |
| 6,240,616 B1 * | 6/2001 | Yan | 29/527.2 |
| 6,254,642 B1 | 7/2001 | Taylor | |
| 6,485,496 B1 | 11/2002 | Suyker et al. | |
| 6,540,775 B1 | 4/2003 | Fischell et al. | |
| 7,500,986 B2 * | 3/2009 | Lye et al. | 623/1.15 |
| 2002/0123790 A1 * | 9/2002 | White et al. | 623/1.14 |
| 2004/0006807 A1 | 1/2004 | Wang | |
| 2004/0006983 A1 | 1/2004 | Sawdon | |
| 2005/0096731 A1 | 5/2005 | Looi et al. | |
| 2006/0122684 A1 | 6/2006 | Lye et al. | |
| 2007/0038288 A1 | 2/2007 | Lye et al. | |

OTHER PUBLICATIONS

Gonschior et al., "Comparison of Local Intravascular Drug Delivery Catheter Systems" American Heart Journal (1995) 130(6):1174-1181.

Hwang et al., "Physiological Transport Forces Govern Drug Distribution for Stent-Based Delivery" Circulation (2001) 104:600-605.

Nakamura et al., "Molecular Strategy Using Cis-Element 'decoy' of E2F Binding Site Inhibits Neointimal Formation in Porcine Balloon-Injured Coronary Artery Model" Gene Therapy (2002) 9:488-494.

Santini et al., "A Controlled-Release Microchip" Nature (1999) 397:335-338.

* cited by examiner

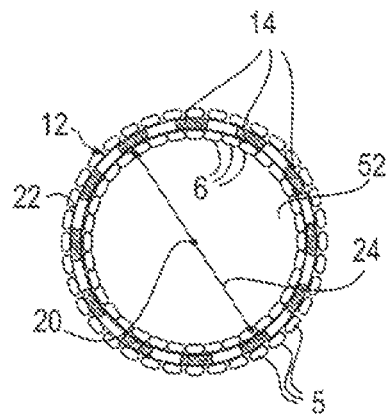
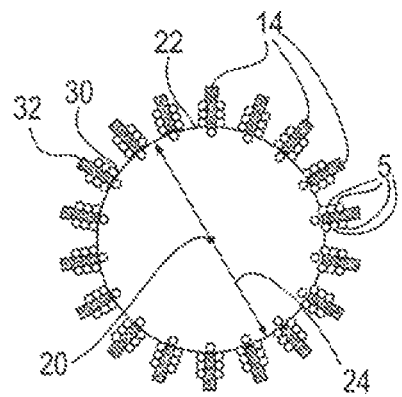
FIG 3A  FIG 3B
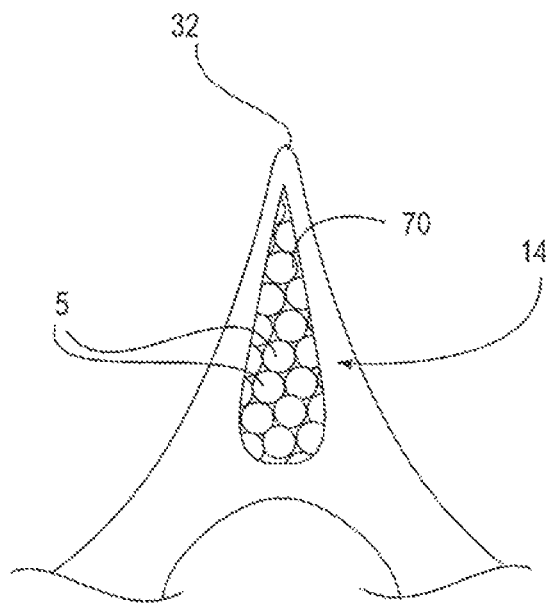
FIG 4

CELL SEEDED EXPANDABLE BODY

CROSS-REFERENCES TO RELATED APPLICATIONS

This application is a continuation of U.S. patent application Ser. No. 10/913,304, filed on Aug. 6, 2004 now abandoned, and claims the benefit and priority of U.S. Provisional Patent Application No. 60/494,045, filed Aug. 7, 2003, the full disclosure of which is hereby incorporated by reference for all purposes.

This application is also a continuation in part of PCT Patent Application No. PCT/US03/21754 filed on Jul. 11, 2003 which claims the benefit and priority of U.S. Provisional Patent Application No. 60/395,180 filed Jul. 11, 2002, and U.S. Provisional Patent Application No. 60/421,404 filed Oct. 24, 2002, the full disclosures of which are hereby incorporated by reference for all purposes.

This application is also a continuation in part of PCT Patent Application No. PCT/US03/21611 filed on Jul. 11, 2003 which claims the benefit and priority of U.S. Provisional Patent Application No. 60/395,180 filed Jul. 11, 2002, U.S. Provisional Patent Application No. 60/421,404 filed Oct. 24, 2002, U.S. Provisional Patent Application No. 60/421,350 filed Oct. 24, 2002, and U.S. Provisional Patent Application No. 60/428,803 filed Nov. 25, 2002, the full disclosures of which are hereby incorporated by reference for all purposes.

STATEMENT AS TO RIGHTS TO INVENTIONS MADE UNDER FEDERALLY SPONSORED RESEARCH AND DEVELOPMENT

This invention was made with government support under grant number R21 HL071976-01 (G. K. Owens, PI) entitled "Derivation of Smooth Muscle Lineages from Stem Cells," awarded by the National Institutes of Health. The government may have certain rights in the invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to apparatuses, systems and methods of treating a patient. Particularly, the present invention relates to treating medical conditions using cell therapy via body lumens. In some instances, the present invention relates to treating a blood vessel, such as in the treatment of heart disease and aneurysms.

1. Heart Disease

Heart disease continues to be a leading cause of death in the United States. The mechanism of this disease is often progressive narrowing of coronary arteries by atherosclerotic plaque which can lead to acute myocardial infarction and disabling angina. Techniques to treat coronary atherosclerosis include percutaneous transluminal coronary angioplasty, (or PTCA, commonly referred to as balloon angioplasty), atherectomy, and coronary stenting. In each of these treatments, compression of the plaque and expansion of the coronary artery, or removal of the atherosclerotic plaque, often restores lumen patency. In stenting, a stent, such as a metal or wire cage-like structure, is expanded and deployed against the plaque.

Despite the overall initial success of these procedures, many patients undergoing these therapeutic procedures to clear blocked coronary arteries will suffer restenosis (re-blockage) at some point after the initial procedure. Such restenosis may be a manifestation of the general wound healing response or may be due to a variety of other factors.

Thus, it would be desired to provide devices, systems and methods which would provide therapeutic benefits to injured or diseased tissue. Such benefits may include reduction of the incidence of restenosis, particularly in blood vessels treated for atherosclerosis. However such benefits may be applicable to any body lumen which suffers from occlusion and possible restenosis. In addition, such benefits may include a reduction in any initial injury induced by intervention, such as by stenting. At least some of these objectives will be met by the embodiments of the present invention.

2. Aneurysms

An aneurysm is the focal abnormal dilation of a blood vessel. The complications which arise from aneurysms can include rupture, embolization, fistularisation and symptoms related to pressure on surrounding structures. Aneurysms are commonly found in the abdominal aorta, being that part of the aorta which extends from the diaphragm to the point at which the aorta bifurcates into the common iliac arteries. These abdominal aortic aneurysms typically occur between the point at which the renal arteries branch from the aorta and the bifurcation of the aorta. When left untreated, an abdominal aortic aneurysm may eventually cause rupture of the aorta with ensuing fatal hemorrhaging in a very short time. High mortality associated with the rupture has led to the development of transabdominal surgical repair of abdominal aortic aneurysms.

A clinical approach to aneurysm repair which is less invasive than conventional transabdominal surgery is known as endovascular grafting. Endovascular grafting typically involves the transluminal placement of a prosthetic arterial graft within the lumen of the artery. The graft may be attached to the internal surface of an arterial wall by means of attachment devices (often similar to expandable stents), one above the aneurysm and a second below the aneurysm. Such attachment devices permit fixation of a graft to the internal surface of an arterial wall without sewing.

It would be desirable, to provide devices, systems and methods that improve the treatment of aneurysms, such as improving fixation of the graft, increased resistance to graft migration and leakage and/or improvements in the characteristics of the surrounding tissue once in place. At least some of these objectives will be met by the embodiments of the present invention.

3. Use of Cell-Based Therapies

Methods have been developed for using pluripotent stem cells for therapeutic applications, including the delivery of therapeutic genes. Pluripotent stem cells appear to have the ability to differentiate into a number of different cell types, including neurons, cardiomyocytes, skeletal muscle, smooth muscle and pancreatic beta cells, to name a few, that are involved in the pathogenesis of many human diseases, such as atherosclerosis, diabetes, hypertension and various others. However, current methods have limitations which preclude the successful use of such pluripotent stem cells in treating various medical conditions.

To begin, a stem cell per se exhibits almost no target tissue selectivity. As such, if stem cells are simply introduced to target tissues by current methods, such as intravenously or by direct injection, a safety concern is the risk that the cells will differentiate into a non-target cell type and disrupt the normal functions in the target tissues. At worst, this may result in tumorigenesis and/or patient mortality. A possible solution is to use stem cells which have been triggered to becoming the target cell type, i.e. progenitor cell types such as smooth muscle progenitor cells. Since these stem-cell derived progenitor cells have started onto the differentiation pathway sufficiently to be "committed" to becoming the desired cell type, there is reduced risk of tumorigenesis or differentiation into an undesired cell type. The drawback to this approach (i.e. the use of progenitor cells) is that the engraftment efficiency is usually inversely related to the extent of cell differentiation. Thus, while the use of stem-cell-derived progenitor cells may reduce or eliminate safety concerns, the fact that the progenitor cells are further down the differentiation pathway as compared to pluripotent stem cells means that their engraftment efficiency is reduced, and this will in turn reduce the likelihood of a clinical benefit.

Alternatively, differentiated somatic cells have been used for cell-based therapies. However, these applications have also been limited by the lack of methods to provide efficient engraftment as described above.

Thus, it would be desirable to provide devices, systems and methods that will deliver therapeutic cells directly to the target site, such that regardless of the extent to which these cells have differentiated, their engraftment into the target site will be significantly improved. At least some of these objectives will be met by the embodiments of the present invention.

4. Immune Issues Related to Use of Non-Autologous Cells

Interest has developed in using non-autologous cells for cell-based therapies, particularly non-autologous embryonic stem cells. Embryonic stem cells may have properties, such as pluripotentiality and infinite replicative life span, that are not obtainable with autologous somatic stem cells. In addition, various non-human cells may be used in the treatment of human diseases, for example, porcine pancreatic beta cells for treatment of diabetes. However, non-autologous and non-human cells are attacked by the patient's immune system, thus limiting their long term efficacy and viability.

Thus, it would be desirable to provide devices, systems and methods that allow the delivery of non-autologous cells to a desired tissue site while simultaneously isolating them from the patient's immune system. This would reduce or prevent any immunologic rejection of the cells. At least some of these objectives will be met by the embodiments of the present invention.

BRIEF SUMMARY OF THE INVENTION

The present invention provides devices, systems and methods for the localized delivery of cells which provide a therapeutic benefit. The cells may include but are not limited to autologous stem cells. Localized delivery is achieved with the use of a stent-like expandable body seeded with cells which is positioned within a body lumen. The expandable body is expanded to contact at least a portion of the inner walls of the body lumen and the cells and/or cellular products are delivered to the surrounding tissue. The therapeutic benefit provided is dependent on the type of cells used and the features of the expandable body, to name a few.

In a first aspect of the present invention, the expandable body may take the form of any of a variety of stents used for placement within body lumens, such as blood vessels. For example, the expandable body may comprise a conventional stent used to treat coronary occlusions, such as described by U.S. Pat. Nos. 6,540,775, 6,113,621, and 4,776,337, each of which is incorporated by reference herein for all purposes. Or, the expandable body may comprise a conventional stent graft used to treat aneurysms, particularly abdominal aortic aneurysms, such as described by U.S. Pat. Nos. 5,824,039 and 5,693,084, each of which is incorporated by reference herein for all purposes.

In other embodiments, the expandable body comprises a device such as provided by Reed et al. (U.S. Pat. No. 6,197,013), incorporated by reference herein for all purposes. The Reed et al. devices include arrays of micromechanical probes present on the surface of the devices which penetrate the body lumen wall and allow for efficient transport of therapeutic agents, such as cells, into the wall. In the specific example of blood vessels, delivery can be effected directly to at least the medial layer of the vessel wall.

In still other embodiments, the expandable body comprises a device having deployable microstructures, such as provided by U.S. Provisional Patent Application No. 60/395,180, U.S. Provisional Patent Application No. 60/421,404, and PCT Application No. PCT/US03/21754, the full disclosures of which are hereby incorporated by reference for all purposes. The microstructures are formed in or attached to the expandable body in a low profile fashion suitable for atraumatic introduction to the body lumen with the use of a catheter or other suitable device. Each microstructure has an end which is attached to the expandable body and a free end. Once the apparatus is positioned within the body lumen in a desired location, the body is expanded and the microstructures deployed to a position wherein the free ends project radially outwardly. The free ends of the deployed microstructures then penetrate the lumen wall by continued expansion of the body. Additionally, a therapeutic agent, such as cells, may be delivered to the lumen wall by the microstructures. When the expandable body comprises a stent, the mechanism may be left in place, the microstructures providing anchoring and sealing against the lumen wall.

In yet other embodiments, the expandable body comprises any of the devices for treating aneurysms described in U.S. Provisional Patent Application No. 60/421,350, U.S. Provisional Patent Application No. 60/428,803 and PCT Application No. PCT/US03/21611, the full disclosures of which are hereby incorporated by reference for all purposes. These devices include a tube which is held in place within the vasculature by at least one expandable body having at least one microstructure. The microstructures are attached to the expandable body in a low profile fashion suitable for atraumatic introduction to the vasculature with the use of a catheter or other suitable device. Each microstructure has an end which is attached to the expandable body and a free end. Once the apparatus is positioned within the vasculature in the desired location, the microstructures are deployed so that the free ends project radially outwardly. The free ends of the deployed microstructures then penetrate the blood vessel wall by continued expansion of the body, holding the tube in place.

It may be appreciated that the expandable body may take the form of any device which is expandable within a body lumen to provide localized delivery of cells and/or cellular products to the body lumen. Various body lumens are found in but are not limited to the vascular system, the pulmonary system, the gastro-intestinal tract, the urinary tract and the reproductive system.

It may be further appreciated that the surface of the expandable body may be porous to allow for a greater retention of therapeutic agents, cells or other substances that may have direct or indirect therapeutic benefits, such as matrix components, growth factors and/or combinations thereof. These substances may promote wound healing or tissue/organ regeneration or repair by augmenting the function of the patient's existing cells or tissues. Some embodiments of such a porous surface are obtained by means of a de-alloying method, preferred embodiments of which have been described in U.S. Provisional Patent Application No. 60/426,106 filed on Nov. 30, 2002, incorporated herein by reference for all purposes. In other embodiments, the porous surface provides controlled release over time of substances that regulate the activity or properties of the cells contained on the device or in proximity to the device. For example, the porous surface may provide controlled release of $TGF_{\beta1}$, a substance known to increase matrix production by smooth muscle cells as well as many other cell types. Such controlled release may be useful in the repair of aneurysms where it is desirable to have cells produce large quantities of extracellular matrix components. In still other embodiments, the porous surface is used to deliver agents that control the activity of a therapeutic gene contained with cells seeded thereon. Such control is achieved by influencing the activity of the therapeutic gene (e.g. through an activation mechanism) or the activity of a promoter-enhancer used to drive expression of the therapeutic gene (e.g. by inclusion of tetracycline or similar responsive elements within the promoter driving the therapeutic gene and inclusion of the inducing agent for that response element in the porous surface).

In a second aspect of the present invention, the cells seeded on the expandable body may be comprised of any cells which provide a therapeutic benefit to the body lumen. Examples of such cells include endothelial cells, pancreatic beta cells, myofibroblasts, cardiac myocytes, skeletal muscle satellite cells, smooth muscle cells, dendritic cells, epithelial cells, multi-potential somatic stem cells and derivatives thereof, embryonic stem cells and derivatives thereof, neuronal cells, glial cells, hepatocytes, and various endocrine cells (e.g. thyroid, parathyroid, adrenal cortex), to name a few.

In some embodiments, genetically modified cells are used to over-express a therapeutic gene. In preferred embodiments, genetically modified smooth muscle cells (SMC) are used. This is because a large number of major human diseases, including coronary artery disease, hypertension, and asthma are associated with abnormal function of SMCs. In addition, SMC dysfunction also contributes to numerous other human health problems including vascular aneurysms, and reproductive, bladder and gastrointestinal disorders. Therefore, a therapeutic effect can be achieved by delivering SMCs which have been genetically modified to over express a therapeutic agent, thereby reducing or eliminating the physiological consequences caused by SMC dysfunction.

Although the present invention relates to the use of a plurality of cell types and sources, one preferred embodiment uses genetically modified stem cells or cells derived therefrom. Stem cells exhibit a virtually infinite replicative lifespan which is beneficial for carrying out genetic engineering methods. Such a lifespan is also beneficial for being able to generate sufficient numbers of cells for clinical applications. This is particularly useful since a patient's own stem cells may often be available in very limited supply, at least without major surgery or patient risk. In contrast, use of somatic differentiated cell populations are limited in that these cells can only undergo a relatively small number of population doublings before senescing.

One preferred embodiment of the present invention is to employ stem cell derived smooth muscle progenitor cells produced using methods described in WO 02/074925, incorporated herein by reference for all purposes. These smooth muscle progenitor cells have been isolated and purified by transforming a population of pluripotent somatic or embryonic stem cells with a DNA construct comprising a smooth muscle specific promoter operably linked to a selectable marker gene.

Delivery of therapeutic genes for treatment of SMC related diseases such as atherosclerosis, asthma, hypertension, etc. In this embodiment of the technology, stem cell derived SM tissues or cells would be genetically engineered to express a desired therapeutic gene or agent and surgically implanted into a desired treatment site in vivo. An example would be implantation of stem cell derived vascular SMC that express high levels of NO synthase into coronary vessels as a means of treating coronary atherosclerosis or re-stenosis.

A major limitation in using these stem cell derived smooth muscle progenitor cells with conventional delivery methods is that the conventional delivery methods do not provide effective engraftment of the cells into the desired tissue site while at the same time reducing or eliminating the risks of delivery to non-target sites. As mentioned, the engraftment potential is highest for undifferentiated cells, however undifferentiated cells pose the greatest risk for tumorigenesis or other undesired side effects. Therefore, a balance between these risks and benefits is desired. Such a balance may be achieved by the use of expandable bodies having micromechanical probes, such as provided by Reed et al. (U.S. Pat. No. 6,197,013), or expandable bodies having deployable microstructures as described above. In this preferred embodiment, the cells are seeded onto the expandable body and delivered directly to specific locations, particularly within the wall of a body lumen. The cells are mechanically embedded into and/or held against the wall of the body lumen which improves engraftment of the cells into the target tissue. This process may be further aided by use of the porous coating to deliver agents that promote engraftment as well as other desired properties of the cells.

In preferred embodiments, genetically modified autologous SMC, adult or embryonic stem cell derived SMC or SMC progenitor cells isolated from the patient's own somatic stem cells are used. In some embodiments, SMC progenitor cells as described in PCT/US02/08402, incorporated herein for all purposes, may be used. Any of these cells may be modified to over-express a possible therapeutic gene, such as endothelial nitric oxide synthase (eNOS) or inducible nitric oxide synthase (iNOS). Nitric oxide (NO) has many actions that could be beneficial to the vascular system, particularly following vascular injury. These include inhibition of platelet deposition and leukocyte adherence, inhibition of vascular smooth muscle cell proliferation and migration, inhibition of endothelial cell apoptosis, stimulation of endothelial cell growth, and vasodilation. Furthermore, inadequate NO production at sites of injury has been shown to contribute to vascular occlusive diseases including atherosclerosis and restenosis following angioplasty, endarterectomy, cardiac bypass surgery, or peripheral vascular bypass surgery. Local delivery of NO to a particular site may be achieved through transfer of an NOS gene, such as eNOS, iNOS, or nNOS, to the site by incorporation into the cells of the cell-seeded expandable body of the present invention. By delivering NOS gene expressing cells to a specific site, NO will be produced at that site without systemic effects. In addition, a porous surface on the expandable body, as described previously, may be used to release co-factors that are known to enhance the biological activity of NOS/NO.

Alternative genes that might be expressed to confer a therapeutic benefit include $TGF_{\beta1}$, which has anti-inflammatory properties and which also has been shown to inhibit SMC growth, promote differentiation, and enhance production of extracellular matrix components. Other possibilities include cytokines IL-4, IL-10 or IL-13 whose anti-inflammatory properties may promote wound repair or regeneration and/or reduced restenosis.

It may be appreciated that genetic modification such as described above may be applied to cells other than SMCs, and these cells may also be used with the cell-seeded expandable body of the present invention. In addition, the methods provided in WO 02/074925, exemplified for the isolation of SMC and smooth muscle progenitor cells, are readily adaptable to the production of any desired cell type by replacing the SMC specific/selective promoter/enhancer of the reporter gene construct with an appropriate promoter regulatory element that is selective/specific for the cell type of interest. Examples include the use of promoter/enhancers specific for cardiac myocytes, endothelial cells and neurons. As an example, cells used in the present invention may be comprised of progenitor cells derived by a method comprising the steps of providing a population of cells comprising totipotent or pluripotent cells, transfecting the population of cells with a nucleic acid sequence comprising a smooth muscle cell specific promoter/enhancer operably linked to a marker, inducing the population of cells to become smooth muscle cells and identifying the smooth muscle progenitor cells based on the expression of the marker.

In other embodiments, cells which have not been genetically modified to over-express a possible therapeutic gene, referred to herein as "unmodified cells", are used. Such cells may be used to augment tissue repair and regeneration. For example, when unmodified autologous SMC, stem cell derived SMC or SMC progenitor cells are used, proliferation of the SMCs and/or associated production of extracellular matrix components including collagen and elastin can rebuild blood vessels. The blood vessels may have been damaged due to traumatic injury, such as by an accident, major reconstructive surgery, or repair of a congenital vascular defect. The SMCs can also be used to rebuild blood vessels which suffer from aneurysms, a progressive vascular abnormality associated with degeneration and dissection of the blood vessel wall and SMC hypocellularity. They may be caused by many factors including extensive atherosclerotic disease, a congenital vascular defect, or mutations in genes important for determining the tensile strength of blood vessels, such as in the case of Marfan's Syndrome which is the result of mutations in the fibrillin gene. In addition, a porous surface on the expandable body may be employed to deliver agents that enhance the desired properties of the unmodified cells. For example, $TGF_{\beta 1}$ may be used since it is known to dramatically enhance matrix production, and/or PDGF BB may be used to promote proliferation of progenitor cells provided on the device as well as recruitment of resident cells that could aid in the repair process.

When the cell-seeded expandable bodies of the present invention are used to treat an aneurysm, the expandable bodies anchor a tube or graft to the vessel walls surrounding an aneurysm. SMCs may be delivered to the vessel walls to increase anchorage of the tube and reduce migration of the tube along the blood vessel. Such migration could lead to leakage, exposure of the aneurysm and damage to the blood vessel, to name a few. In addition, the improved anchorage may also prevent apparent migration of the apparatus which occurs when the aneurysmal sac grows in size and as such encroaches upon the ends of the apparatus. This results in a reduction of the distance between the terminus of the apparatus and the aneurysm which is the same effect as migration. Thus, the SMCs help maintain intimate contact between the apparatus and the vessel wall and prevent aneurysmal sac growth. The SMCs can also be delivered to the blood vessel lumen, the blood vessel walls and/or the outer surface of the blood vessel to encourage tissue regrowth or extra-cellular matrix formation. The SMCs may also be delivered to the aneurysmal sac. This may allow for tissue regrowth within the sac, strengthening the tissue within the aneurysmal walls. In addition, as noted above, a porous surface on the device may be employed to deliver agents to enhance the repair or regenerative process.

SMCs may also be employed in reconstructive surgery of the gastrointestinal tract, urinary tract, or other tissues in which SMC are a predominant cell type. Other cell types may also be used to rebuild other types of tissues. For example, autologous stem cell derived cell types may be used to enhance wound healing, bone repair, musculo-skeletal repair following traumatic injury or disease, tissue engineering, and replacement of degenerative or senescent cells, to name a few.

BRIEF DESCRIPTION OF THE DRAWINGS

FIGS. 3A-3B provide a schematic illustration of the embodiments of FIGS. 2A-2B with cells seeded thereon.

FIG. 4 illustrates a microstructure having cells seeded within an internal lumen of a microstructure.

DETAILED DESCRIPTION OF THE INVENTION

It may be appreciated that any combination of the above described cell types and expandable body types may be used. However, for clarity of description, cells will mainly be described and illustrated as generic "cells" representing any of the described cell types. In addition, the expandable bodies will mainly be described and illustrated as comprising a device having deployable microstructures. However, this is not intended to limit the scope of the invention as the features provided may apply to any of the expandable body types.

Overview

Figure 1:
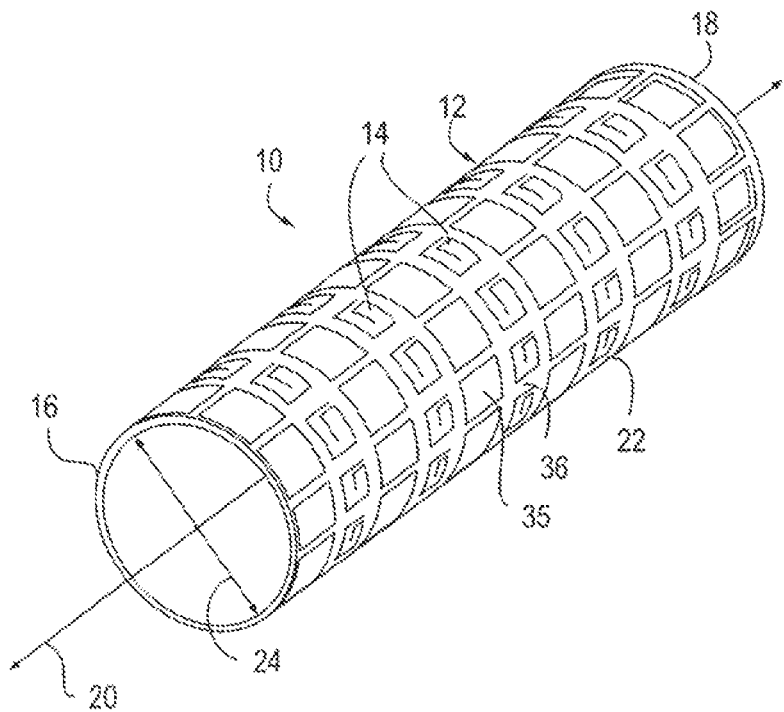
FIG. 1 is a perspective view of an embodiment of an apparatus of the present invention comprising an expandable body and at least one microstructure.

Referring to FIG. 1, an embodiment of an apparatus 10 of the present invention is illustrated, the apparatus 10 comprises an expandable body 12 and at least one microstructure 14. The expandable body 12 has a proximal end 16, a distal end 18, a longitudinal axis 20 therebetween. A cross-sectional diameter 24 is also shown. In this embodiment, the expandable body 12 comprises a cylindrical structure surrounding the longitudinal axis 20. However, it may be appreciated that the expandable body 12 can comprise any shaped structure, including oval, hemispherical, ellipsoidal, spherical, square, rectangular, or polygonal, to name a few, and may be symmetrical or non-symmetrical. Further, the expandable body 12 may be sized and shaped for delivery from a catheter or other suitable device for positioning within a body lumen. The embodiment of FIG. 1 is suitable for permanent placement within the body lumen, such as to resemble a conventional vascular stent.

Together, the microstructures 14 and the expandable body 12 form the cylindrical structure surrounding the longitudinal axis 20. FIG. 1 illustrates the apparatus 10 in an unexpanded state wherein the microstructures 14 are in an undeployed position. Here, the microstructures 14 are preferably aligned or flush with an outer surface 22 of body 12 so that the surface 22 does not include substantial protrusions. Alternatively, the microstructures 14 may be positioned below the surface 22.

Figure 2A:
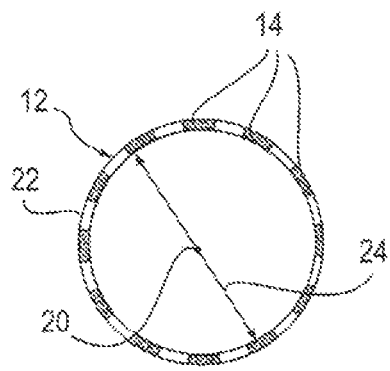
FIGS. 2A-2B provide cross-sectional views of the apparatus of FIG. 1 in the unexpanded and expanded states, respectively.
Figure 2B:
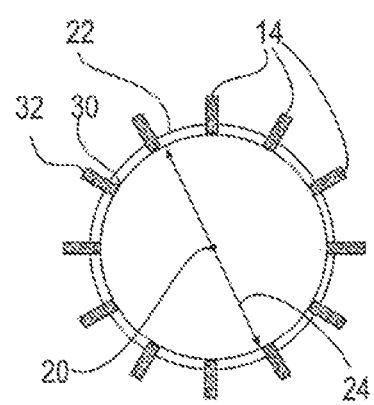

FIGS. 2A-2B provide cross-sectional views of the apparatus 10 of FIG. 1 in the unexpanded and expanded states, respectively. FIG. 2A shows the wall of the body 12 within which lie microstructures 14, highlighted by shading. Thus, when the expandable body 12 is in the unexpanded state, the microstructures 14 are in an undeployed position which is aligned with the surface 22. FIG. 2B illustrates the expandable body 12 in an expanded state wherein the cross-sectional diameter 24 is increased. Here, the microstructures 14 are in a deployed position wherein a free end 32 of each microstructure 14 projects radially outward from the longitudinal axis 20 while an attached end 30 remains attached to the body 12. In some embodiments the mechanical act of expansion of the body 12 creates forces which deploy the microstructures 14. It may be appreciated that the deployed microstructures 14 may form any angle with the surface 22, including a substantially 90 degree angle as shown. Further, different microstructures 14 may form different angles, angles may vary randomly or in a pattern, angles may be selectable particularly based on amount of expansion, and some microstructures may not deploy while others deploy. Any spacing between the microstructures 14 may also be used, preferably between 5 microns and 10,000 microns. Deployed microstructures have heights which may vary but are typically sufficient to penetrate the lumen wall to a desired depth. In a blood vessel, this may include traversal of the thickness of any atherosclerotic plaque lining the vessel wall. Thus, the deployed microstructures may have heights which vary from less than 25 μm to over 5000 μm.

As illustrated in FIG. 1, the expandable body 12 may comprise a series of interconnected solid sections 36 having spaces 35 therebetween. In preferred embodiments, the expandable body 12 comprises an endoluminal stent. Although such stents may be introduced into various body lumens, such as within the pulmonary system, the gastrointestinal tract, the urinary tract and the reproductive system, to name a few, conventional stents are commonly used in the vascular system, particularly the coronary arteries. Conventional vascular stents are typically formed from wires bent or woven to define a series of relatively tightly spaced convolutions or bends or from a solid metal structure from which portions are removed in a selected pattern. The expandable body 12 of the present invention may resemble conventional stents and may be similarly manufactured. For example, the expandable body 12 can be laser machined from annealed 316L tubing; electric discharge machining (EDM) or electrochemical etching can also be used to fabricate the devices, to name a few. The particular design of the structure is dependent upon the microstructures and the way that they deploy upon expansion of the body 12. Examples of such designs will be provided in later sections.

Cell Seeding of Expandable Body

The expandable body 12 is seeded with the desired cells by any suitable method. Typically the cells are mixed with whole blood or tissue culture media and incubated with the expandable body 12. The incubation time will be sufficient to provide desired cell retention upon the body 12. In some embodiments, the incubation time will be sufficient to generate a confluent monolayer of cells on the surfaces of the expandable body 12. Various methods of cellular application may be used, including rotating the expandable body 12 about cell-rich seeding suspensions, application of an external vacuum or use of surface electrocharging to improve seeding efficiency, adhesion strength and uniformity. In addition, the expandable body 12 may be coated with a substance or substrate prior to seeding to improve ultimate seeding efficiency. The substances may comprise polymer substrates, biocompatible proteins, growth factors, extracellular matrix components, or a combination of these.

To increase the ability of the cells 5 to be seeded on the microstructures 14, the structural material of the expandable body 12 may have a porous surface. This may allow any substances which are used to more highly bond with the expandable body 12. This may in turn increase the retention of the cells 5. In one embodiment pores are created by anodizing the metal forming the apparatus or coating the metal with a material which is then anodized. Anodization produces a high density of small, vertically oriented pores, of which the size and configuration can be controlled by varying the anodization current, temperature and solution concentration. If the pores are of sufficient size in relation to the cells 5, the cells 5 may seed within the pores themselves allowing even greater retention. In other embodiments, a porous coating is created by depositing a precursor alloy onto the expandable body followed by a de-alloying procedure. The de-alloying procedure chemically or electrochemically removes one or more components of the precursor alloy leaving behind a nanoporous matrix. Embodiments of such a method have been described in U.S. Provisional Patent Application No. 60/426,106 filed on Nov. 30, 2002, incorporated herein by reference for all purposes.

In these and other embodiments, the porous surface may comprise a controlled release porous coating which provides time dependent release of various substances. When the coating comprises a nanoporous metallic coating, the coating may have a morphology that provides the controlled time dependent release of various substances. One or more substances may be used to regulate the activity or properties of the cells on the expandable body or in proximity to the expandable body. For example, the substances may promote cell adherence and/or cell growth. An example of such a substance is a member of the $TGF_\beta$ family, such as $TGF_{\beta1}$ which is known to dramatically increase matrix production by smooth muscle cells as well as other cell types. Release of $TGF_{\beta1}$ in a controlled manner is useful in the repair of aneurysms where it is desirable to have cells produce large quantities of extracellular matrix components. Other substances may augment growth of endothelial cells and/or smooth muscle cells. Example substances include VEGF, bFGF, PLGF, and PDGF. Or, one or more substances may be used to control the activity of a therapeutic gene (e.g. through an activation mechanism) or the activity of a promoter-enhancer used to drive expression of the therapeutic gene (e.g. by inclusion of tetracycline or similar responsive elements within the promoter driving the therapeutic gene and inclusion of the inducing substance for that response element in the porous coating).

FIGS. 3A-3B provide cross-sectional views of the apparatus 10 of FIG. 1 in the unexpanded and expanded states, respectively, wherein the apparatus is seeded with cells 5. The size, shape and deposition of the cells 5 have been exaggerated and simplified for clarity of illustration. FIG. 3A shows the wall of the body 12 within which lie microstructures 14, highlighted by shading. Thus, when the expandable body 12 is in the unexpanded state, the microstructures 14 are in an undeployed position which is aligned with the surface 22. The expandable body 12 is shown having cells 5 deposited along an interior lumen 52 and along the outer surface 22, however it may be appreciated that the cells 5 may be deposited on select surfaces, such as the outer surface 22 only or particular portions of the outer surface 22. Since the microstructures 14 are formed in the wall of the body 12, the microstructures 14 are also seeded with cells 5. FIG. 3B illustrates the expandable body 12 in an expanded state wherein the cross-sectional diameter 24 is increased. Here, the microstructures 14 are in a deployed position wherein a free end 32 of each microstructure 14 projects radially outward from the longitudinal axis 20 while an attached end 30 remains attached to the body 12. As shown, the cells 5 are located on various surfaces of the microstructures 14, ready for delivery to the tissue upon penetration by the microstructures 14.

Alternatively, as illustrated in FIG. 4, the cells 5 may be held in one or more internal lumens 70 within the microstructures 14. Here, the free end 32 has a pointed shape. It may be appreciated that the internal lumen 70 may be of any size or shape within the microstructure 14, and may be an isolated lumen or a lumen which extends continuously from microstructure to microstructure. The cells 5 may be in suspension or grown on a surface of the internal lumen 70, such as forming a monolayer, ready for delivery to the tissue upon penetration by the microstructures 14. Positioning of the cells within the microstructures provides a variety of benefits. To begin, the microstructures protect the cells within from dislodgement during handling of the device, during delivery of the device and during deployment of the microstructures 16. Penetration of the tissue by the microstructures 16 positions the free ends 32 of the microstructures 16 within the tissue, allowing direct delivery of the cells 5 to a location within the tissue. In addition, the microstructures 16 may serve to immunoisolate the cells 5 from the surrounding tissue. For example, embryonic stem cells may be positioned within the internal lumens 70 of the microstructures 16 so as to avoid any potential immune reaction from the tissue. The stem cells may then produce a therapeutic agent for delivery from the microstructures 16 without the cells themselves contacting the tissue. Or, a nanoporous membrane may be incorporated into the microstructures to provide immunoisolation of the cells therein. The nanoporous membrane may function similarly to the nanoporous membranes described in T. A. Desai, et al.: Nanopore Technology for Biomedical Applications. J. of Biomedical Microdevices, 1999, 2 (1) 11-4, incorporated herein by reference for all purposes. The nanoporous membranes may be incorporated into the microstructures in a manner similar to the incorporation of dialysis membranes into microfabricated needles as described in J. D. Zahn, et al.: An Integrated Microfluidic Device for the Continuous Sampling and Analysis of Biological Fluids. Proceedings of 2001 ASME International Mechanical Engineering, Congress and Exposition, Nov. 11-16, 2001, New York N.Y., pp. 1-6, incorporated herein by reference for all purposes. Thus, the nanoporous membranes permit the transport of cellular products out of the microstructures and into the penetrated vessel wall, also allowing the in-flow of nutrients to the embedded cells while effectively screening these cells from the patient's immune system. This allows, for example, the use of xenografts and embryonic stem cells while reducing risk of immunorejection by the patient.

Microstructures

Figure 5A:
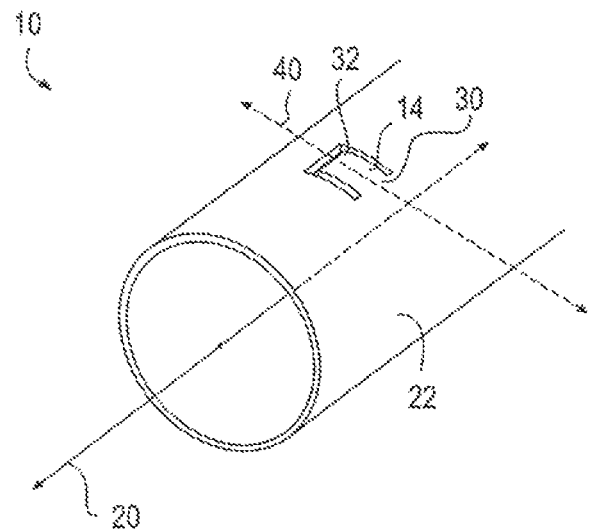
FIGS. 5A-5B, 6A-6B illustrate possible relationships of the directional axis of the microstructure to the longitudinal axis of the body.
Figure 5B:
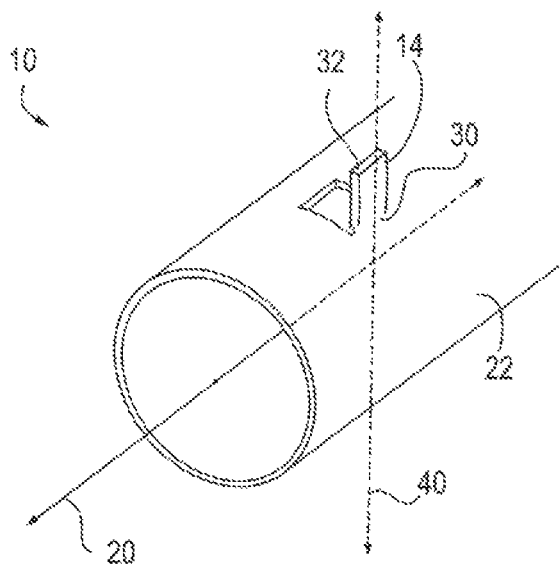
Figure 6A:
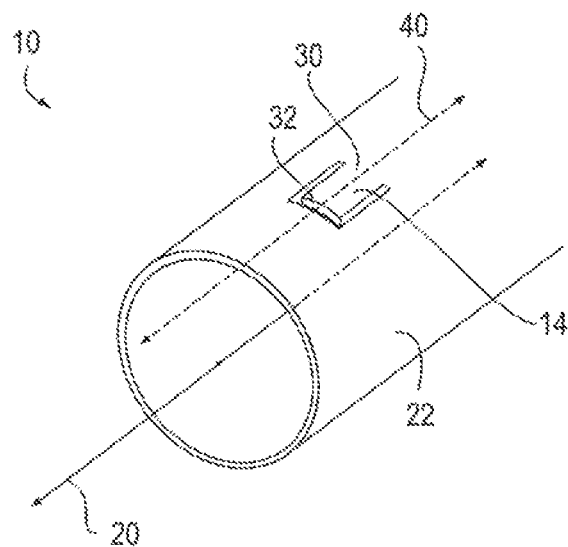

As mentioned, each microstructure 14 has an attached end 30, attached to the body 12, and a free end 32, both in the deployed and undeployed positions. In preferred embodiments, each microstructure has a directional axis 40, such as shown in FIG. 5A, between the free end 32 and the attached end 30. In some embodiments of the apparatus 10, the directional axis 40 extends across the longitudinal axis 20 at an angle while the microstructure 14 is in the undeployed position. Here, the directional axis 40 is shown to form an angle of approximately 90 degrees with the longitudinal axis 20. Deployment of the microstructure 14 projects the free end 32 radially outwardly from the longitudinal axis 20, as shown in FIG. 5B, so that the microstructure 14 extends beyond the surface 22. Alternatively, in some embodiments, the directional axis 40 extends along the longitudinal axis 20 while the microstructure 14 is in the undeployed position, as illustrated in FIG. 6A. In this case, deployment of the microstructure 14 also projects the free end 32 radially outward from the longitudinal axis 20, as shown in FIG. 6B, so that the microstructure 14 extends beyond the surface 22.

Generally, the expandable body 12 comprises a series of interconnected solid sections having spaces therebetween. The solid sections form the structure of the expandable body 12 and form the microstructures 14. In most embodiments, each microstructure has at least a first support and a second support and a free end, the first and second supports being affixed to associate first and second adjacent portions of the radially expandable body. Expansion of the expandable body effects relative movement between the associated first and second portions of the expandable body. For example, the relative movement of the associated first and second portions of the expandable body may comprise circumferential movement of the first portion relative to the second portion when the expandable body expands radially. Although this relative movement may be in any direction, typically the relative movement comprises moving the associated first and second portions apart. Often the circumferential movement pulls the affixed ends of the first and second supports apart, which in turn moves the free end. Thus, such relative movement deploys the microstructures from an undeployed position along the expandable body to a deployed position with the free end projecting radially outwardly from the longitudinal axis. A variety of embodiments are provided to illustrate these aspects of the present invention.

Figure 6B:
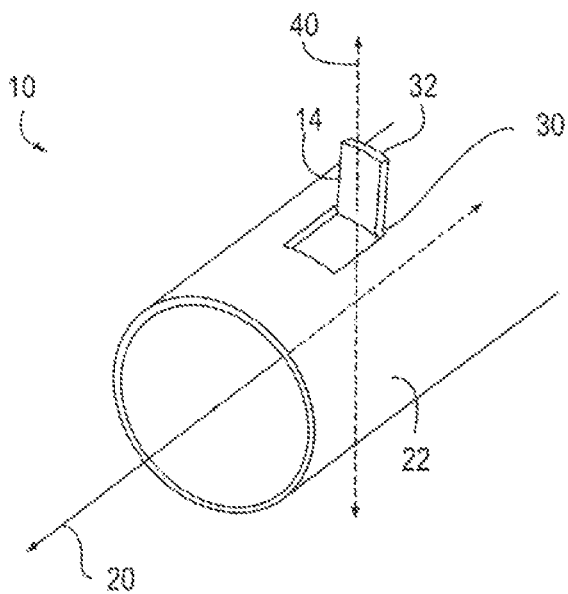
Figure 7:
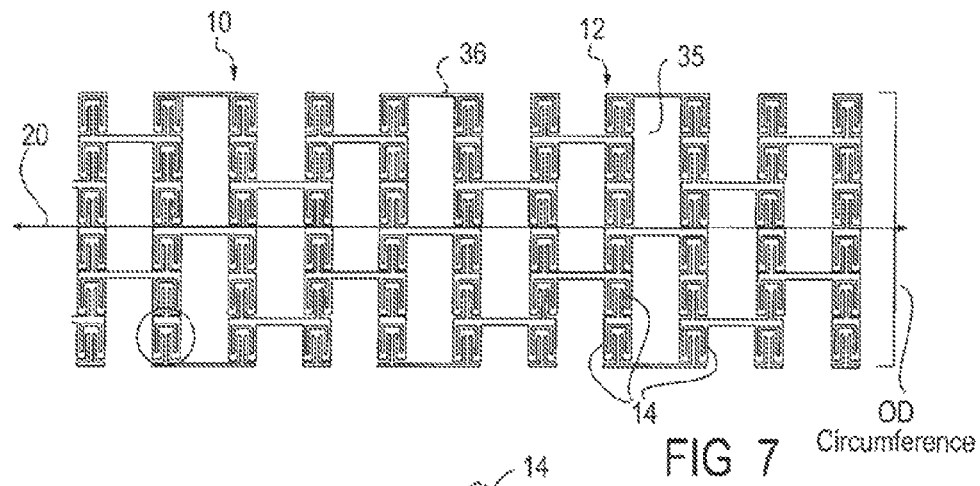
FIG. 7 illustrates an embodiment of the apparatus wherein the microstructures are aligned as in FIGS. 5A-5B, and FIG. 7A provides an exploded view of a microstructure of FIG. 7.
Figure 8A:
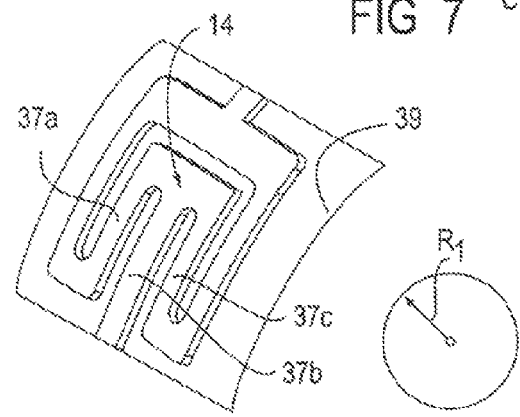
FIGS. 8A-8B shows the microstructure of FIG. 7A in an undeployed and deployed position, respectively.

FIG. 7 illustrates an embodiment of the apparatus 10 wherein the microstructures 14 are oriented as in FIGS. 6A-6B. Thus, although the apparatus 10 is illustrated in a flat plane, it is formed cylindrically around longitudinal axis 20 in this embodiment. As shown, the body 12 comprises a series of interconnected solid sections 36 having spaces 35 therebetween. A portion of the apparatus 10 including a microstructure 14 is illustrated in exploded view in FIG. 7A. Here, a first support 37a, a second support 37b and a third support 37c are shown, each comprising elongate shafts, wherein the second support 37b is disposed longitudinally between the first support 37a and third support 37c. The first, second, and third supports 37a, 37b, 37c are attached to the free end 32 and to first, second and third adjacent portions 38a, 38b, 38c, respectively, of the expandable body, as shown. FIG. 8A shows the microstructure 14 of FIG. 7A wherein the supports 37a, 37b, 37c are adjacent to each other and aligned with a circumference 39 of the expandable body 12 in the undeployed position. Here, the body 12 is in the unexpanded state, wherein the cross-sectional diameter has a radius $R_1$. FIG. 8B shows the body 12 is in the expanded state, wherein the cross-sectional diameter has a larger radius $R_2$. Such expansion draws the first and second associated portions 38a, 38b, apart while the associated third portion 38c moves in unison with the associated first portion 38a. Thus, the supports 37a, 37b, 37c pull the free end in opposite directions forming a tripod structure which causes the free end to project radially outwardly, as shown.

Figure 7A:
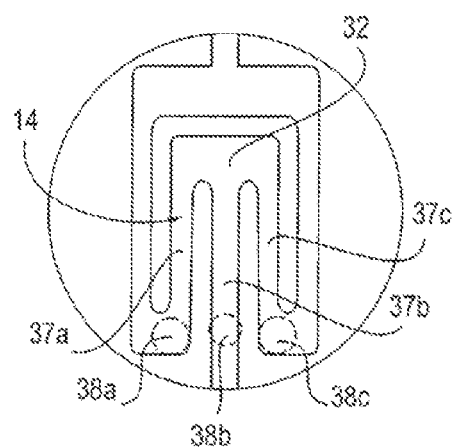
Figure 8B:
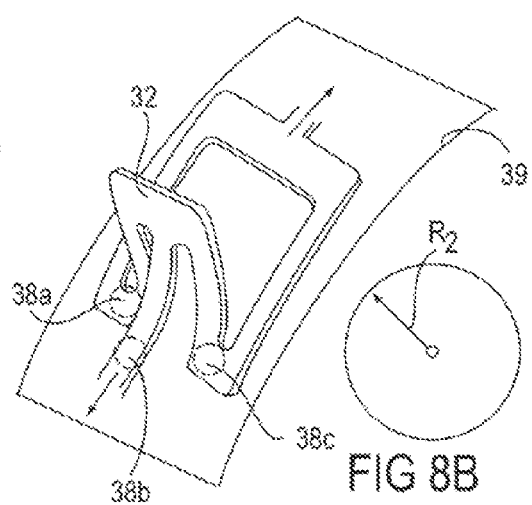
Figure 9A:
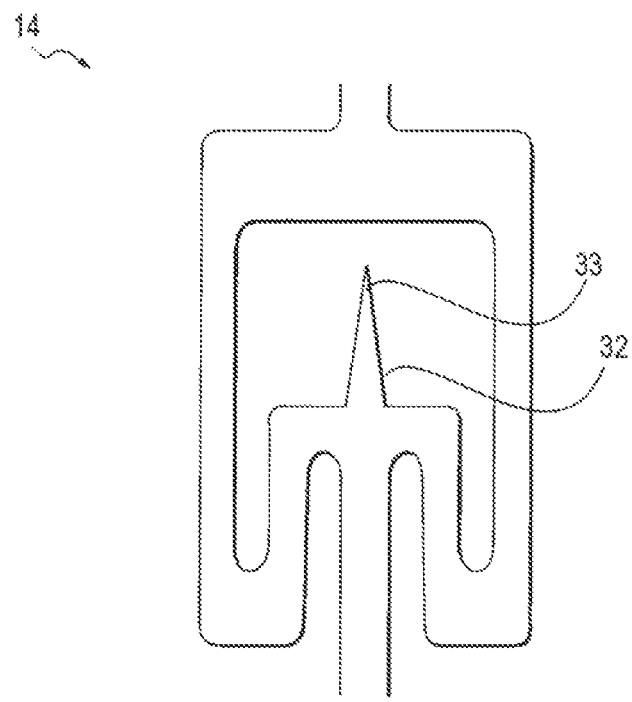
FIGS. 9A-9C illustrate embodiments of the free ends of the microstructures of FIG. 7A.
Figure 9B:
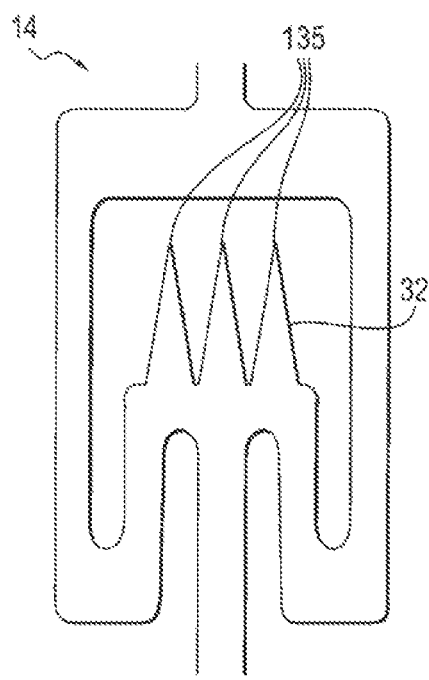
Figure 9C:
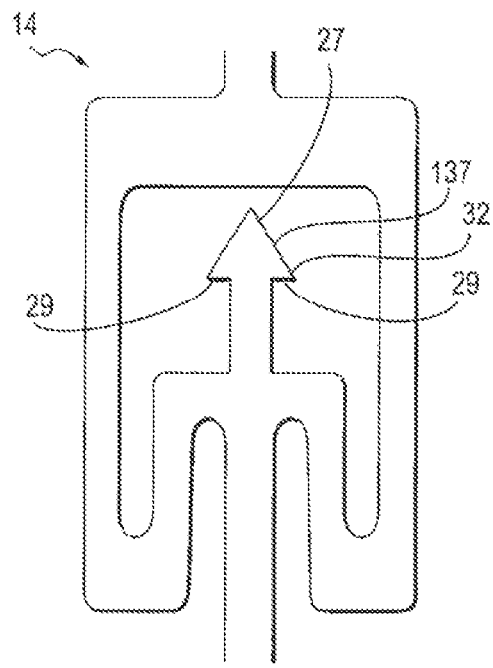

The free ends 32 of the microstructures 14 depicted in FIG. 7 and FIG. 7A are each shown to have a flat-edged shape. However, the free ends 32 may have any desired shape. For example, FIGS. 9A-9C illustrate additional embodiments of microstructures 14 having different shaped free ends 32. In each of these embodiments, the free ends 32 have a pointed shape. When the apparatus 10 is positioned in a body lumen, such as a blood vessel, the pointed shapes of the free ends 32 may assist in penetration of the lumen wall. The shape, size and tapering of each point may possibly guide the free end 32 to a certain penetration depth, such as to a specified tissue layer. In FIG. 9A, the free end 32 has a single point 33 and in FIG. 9B the free end 32 has multiple points 135. In FIG. 9C, the free end 32 has an arrow-shaped point 137. The arrow-shaped point 137 includes a pointed tip 27 and at least one undercut 29 to reduce the ability of the free end 32 from withdrawing from a lumen wall once penetrated. This may be useful when the microstructures are used for anchoring. It may be appreciated that microstructures 14 throughout the apparatus 10 may all have the same free end 32 shape or the shapes may vary randomly or systematically.

Figure 10A:
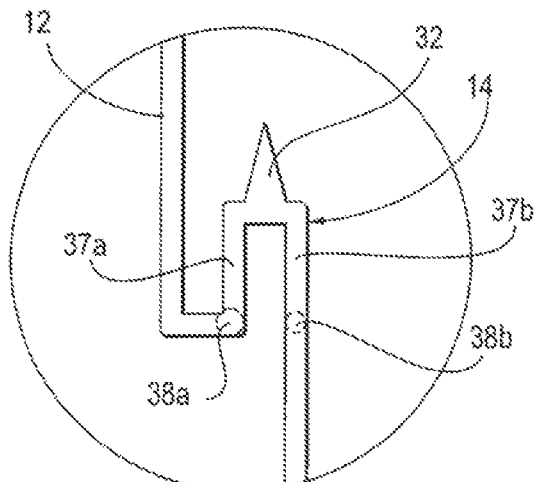
FIGS. 10A-10C illustrate an additional embodiment of the microstructures.
Figure 10B:
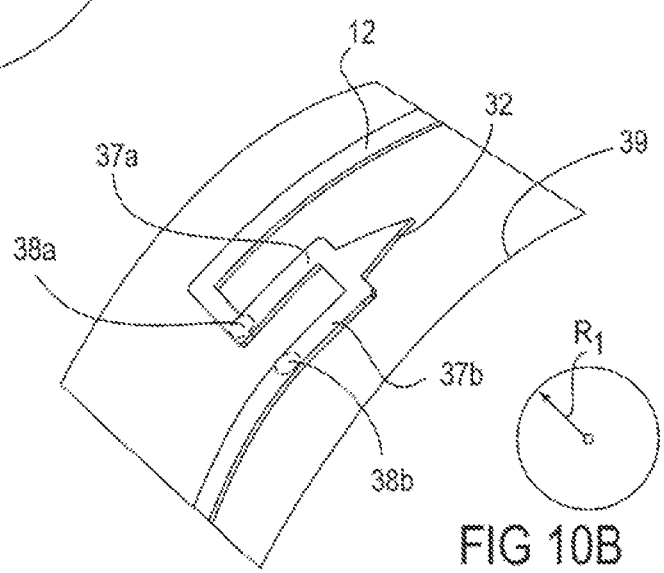
Figure 10C:
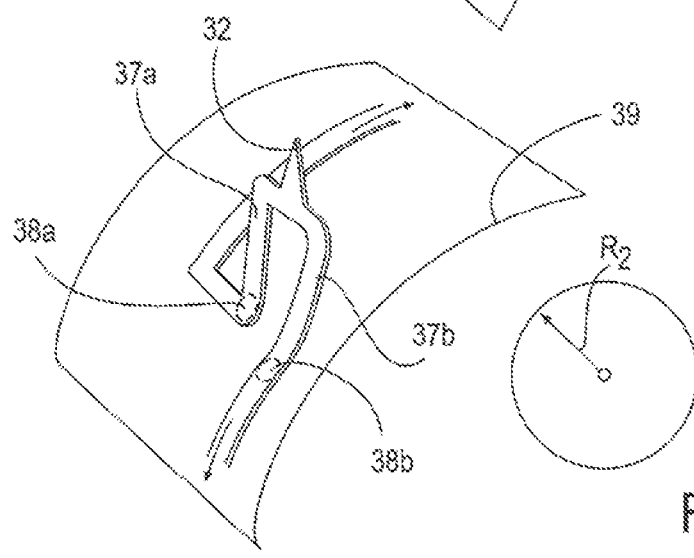

FIG. 10A also illustrates an embodiment of the apparatus 10 wherein the microstructures 14 are oriented as in FIGS. 5A-5B. FIG. 10A provides a portion of the apparatus 10 including the microstructure 14 in exploded view. In this embodiment, the microstructure 14 has first and second supports 37a, 37b and a free end 32, the supports 37a, 37b affixed to associate first and second adjacent portions 38a, 38b of the radially expandable body 12. FIG. 10B shows the microstructure 14 of FIG. 10A wherein the supports 37a, 37b are adjacent to each other and aligned with a circumference 39 of the expandable body 12 in the undeployed position. Here, the body 12 is in the unexpanded state, wherein the cross-sectional diameter has a radius $R_1$. The first and second supports 37a, 37b comprise elongate shafts extending between the free end 32 and the associated first and second adjacent portions 38a, 38b of the radially expandable body 12. FIG. 10C shows the body 12 is in the expanded state, wherein the cross-sectional diameter has a larger radius $R_2$. As shown, relative movement of the associated first and second portions 38a, 38b of the expandable body moves the associated first and second portions 38a, 38b apart so that the supports 37a, 37b pull the free end in opposite directions causing the free end 32 to project radially outwardly.

It may be appreciated that although the free end 32 is illustrated to have a pointed shape, the free ends 32 may have any desired shape, including the shapes illustrated in FIGS. 9A-9C. And, it may also be appreciated that microstructures 14 throughout the apparatus 10 may all have the same free end 32 shape or the shapes may vary randomly or systematically.

Figure 11:
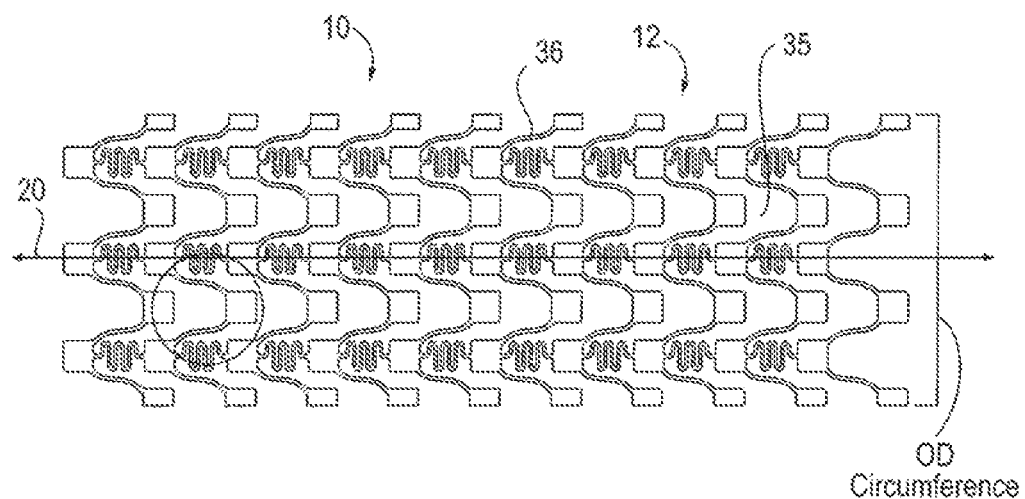
FIG. 11 illustrates an embodiment of the apparatus wherein the microstructures are aligned as in FIGS. 6A-6B, and FIG. 11A provides an exploded view of a microstructure of FIG. 11.
Figure 11A:
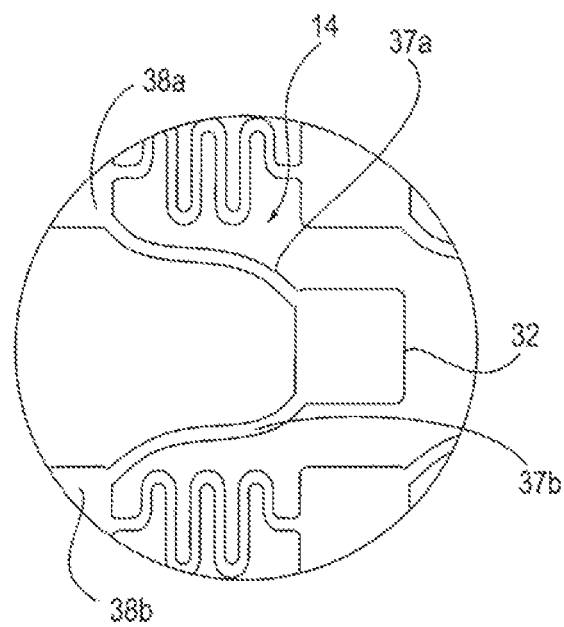

FIG. 11 illustrates an embodiment of the apparatus 10 wherein the microstructures 14 are oriented as in FIGS. 6A-6B. Thus, although the apparatus 10 is illustrated in a flat plane, it is formed cylindrically around longitudinal axis 20 in this embodiment. As shown, the expandable body 12 comprises a series of interconnected solid sections 36 having spaces 35 therebetween. A portion of the body 12 including a microstructure 14 is illustrated in exploded view in FIG. 11A. Each microstructure has a first support 37a, a second support 37b and a free end 32. The supports 37a, 37b are affixed to associate first and second adjacent portions 38a, 38b of the radially expandable body.

Figure 12A:
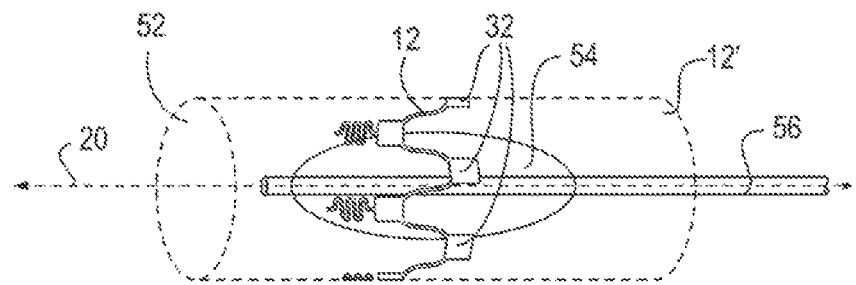
FIG. 12A illustrates a representative portion of the radially expandable body having a cylindrical shape and FIGS. 12B-12C illustrate the movement of the expandable body, particularly the movement of the free ends of the microstructures as the expandable member radially expands the body.
Figure 12B:
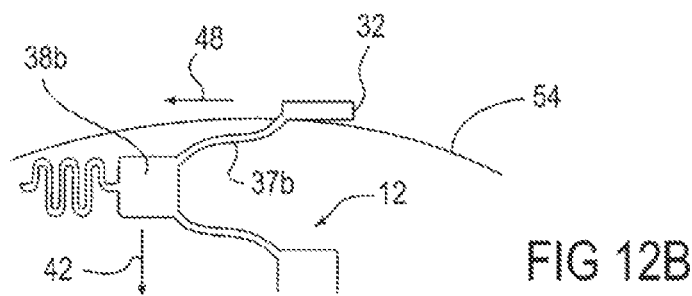
Figure 12C:
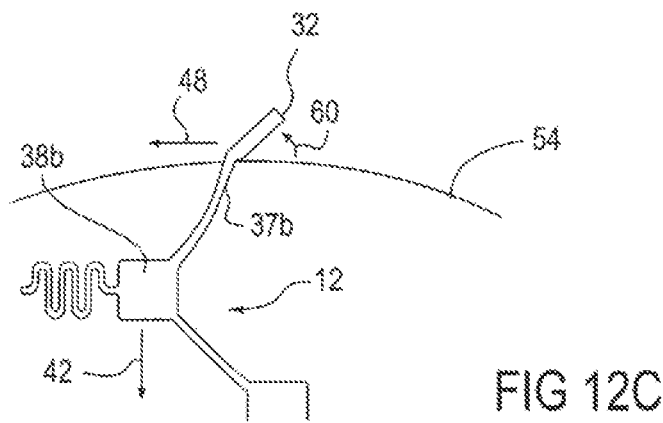

FIG. 12A illustrates a representative portion of the radially expandable body 12 having a cylindrical shape, the remainder of the body illustrated by dashed body 12'. In this embodiment the radially expandable body 12 further comprises an interior lumen 52 along the longitudinal axis 20. The interior lumen 52 may be configured for receiving an expandable member 54 which expands the expandable body 12, as illustrated. In this case, the expandable member 54 is typically mounted on a catheter 56. FIGS. 12B-12C illustrate the movement of the expandable body, particularly the movement of the free ends 32 of the microstructures 14 as the expandable member 54 radially expands the body 12. FIG. 12B is a side view of a portion of the expandable body 12, including a microstructure 14, mounted on expandable member 54. Expansion of the expandable member 54 effects relative movement between the associated first and second portions 38a, 38b, in this case such expansion effects circumferential movement. Circumferential movement is indicated by arrow 42. It may be appreciated that the associated first portion 38a is not shown in FIG. 12B since FIG. 12B is a side view and portion 38a would be located symmetrically on the backside of the expandable member 54. The circumferential movement pulls the affixed ends of the first and second supports 37a, 37b apart which moves the free end 32, indicated by arrow 48. As shown in FIG. 12C, such movement of the free end 32 projects the free end 32 radially outwardly, as indicated by arrow 60. Such projection may be due to friction created between the free end 32 and the expandable member 54 as the expandable member 54 expands the expandable body 12. Alternatively, such projection may be due to other factors, such as the direction of movement of the supports 37a, 37b, the shape of the supports 37a, 37b, or a combination of factors.

It may be appreciated that the expandable body 12 of FIGS. 12A-12C may alternatively be expanded by means other than expansion by an expandable member 54. For example, the expandable body 12 may be self-expanding, as previously mentioned. In this situation, the expandable body 12 is preformed so that deployment of the body 12 allows the body 12 to self-expand toward a predetermined configuration. Preforming may be achieved with the use of an expandable member 54, wherein the body 12 is set while surrounding an expandable member 54 so as to later form this configuration. When the expandable body 12 expands within the body, projection of the microstructures may be due to torquing or movement of the supports 37a, 37b, for example.

Figure 13A:
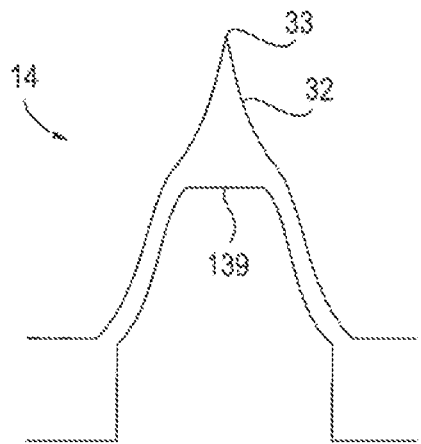
FIGS. 13A-13C illustrate embodiments of the free ends of the microstructures of FIG. 11A.
Figure 13B:
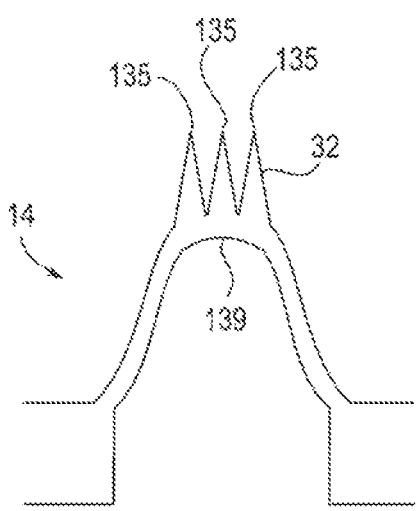
Figure 13C:
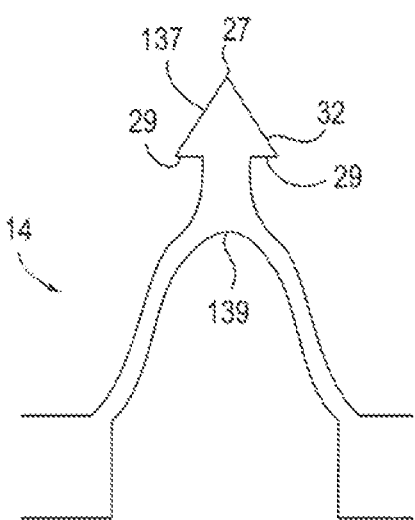

The free ends 32 of the microstructures 14 depicted in FIGS. 11, 11A, 12A-12C are each shown to have a flat-edged shape. However, the free ends 32 may have any desired shape. For example, FIGS. 13A-13C illustrate additional embodiments of microstructures 14 having different shaped free ends 32. In each of these embodiments, the free ends 32 have a pointed shape. When the apparatus 10 is positioned in a body lumen, such as a blood vessel, the pointed shapes of the free ends 32 may assist in penetration of the lumen wall. The shape, size and tapering of each point may possibly guide the free end 32 to a certain penetration depth, such as to a specified tissue layer. In FIG. 13A, the free end 32 has a single point 33 and in FIG. 13B the free end 32 has multiple points 135. In FIG. 13C, the free end 32 has an arrow-shaped point 137. The arrow-shaped point 137 includes a pointed tip 27 and at least one undercut 29 to reduce the ability of the free end 32 from withdrawing from a lumen wall once penetrated. This may be useful when the microstructures are used for anchoring. It may be appreciated that microstructures 14 throughout the apparatus 10 may all have the same free end 32 shape or the shapes may vary randomly or systematically. Likewise, the free end 32 may have a flat-shaped inner edge 139, as illustrated in FIG. 13A, to maximize friction against an expandable member 54 or the free end 32 may have various other shaped inner edges 139, as illustrated in FIGS. 13B-13C.

Figure 13D:
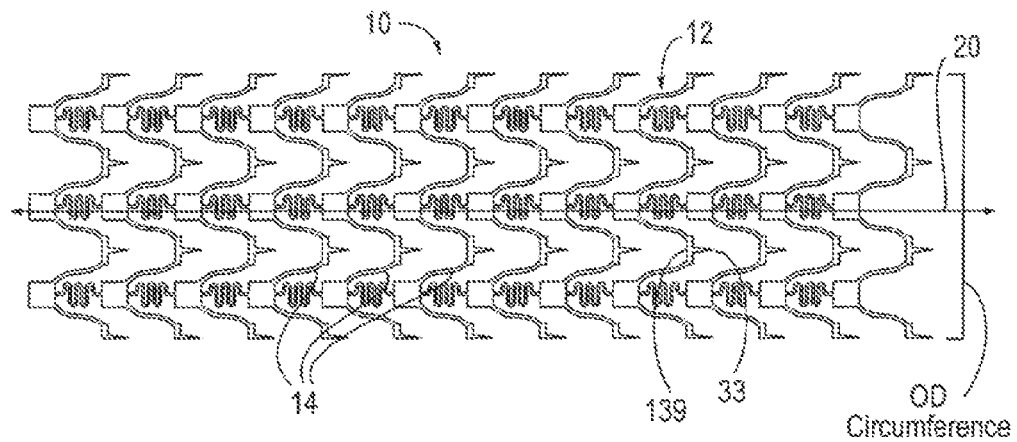
FIGS. 13D-13G illustrate embodiments of the apparatus having various designs.
Figure 13E:
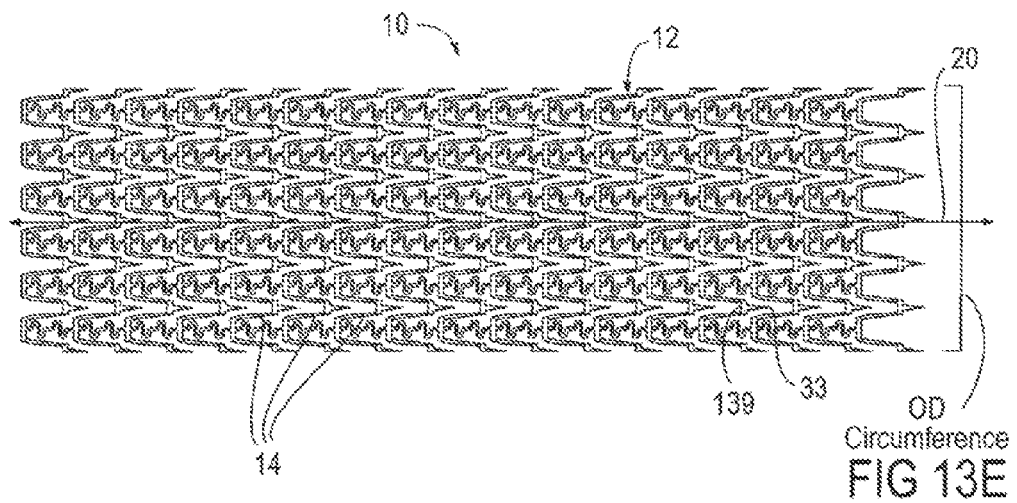
Figure 13F:
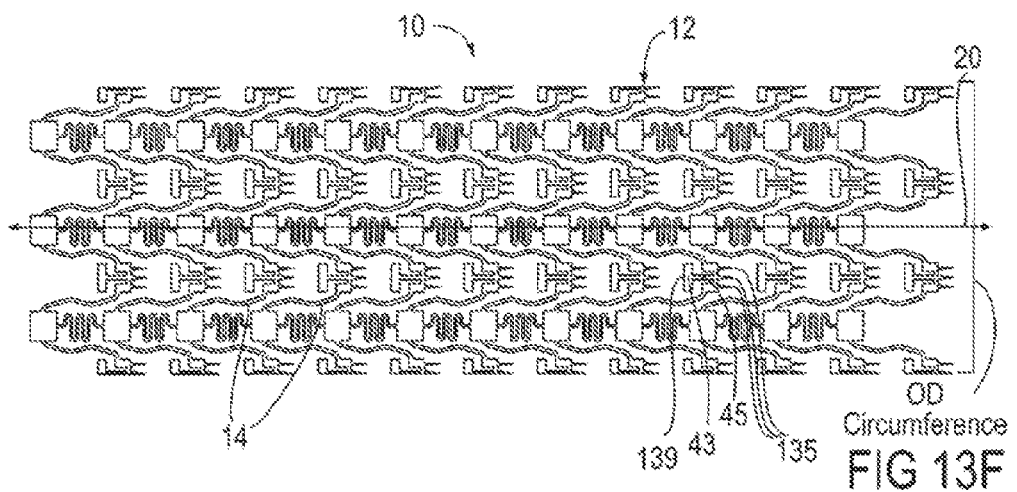

FIGS. 13D-13F illustrate embodiments of the apparatus 10 having various designs. Again, although the apparatus 10 is illustrated in a flat plane, it is formed cylindrically around longitudinal axis 20 in each embodiment. In FIG. 13D, the microstructures 14 have free ends 32 which are shaped as a single point 33 and include a flat inner edge 139. Thus, the free ends 32 are similar to the embodiment illustrated in FIG. 13A. FIG. 13E also illustrates an embodiment wherein the microstructures 14 have free ends 32 which are shaped as a single point 33 and include a flat inner edge 139. However, in this embodiment, the microstructures 14 are positioned more closely together, in a denser pattern. In FIG. 13F the microstructures 14 have free ends 32 which are shaped to have multiple points 135 and to include a flat inner edge 139. In addition, the flat inner edge 139 is part of a flange 43 which is directed opposite of the points 135. The flange 43 provides a wide flat inner edge 139 to maximize friction against an expandable member 54 and a narrow neck region 45 to enhance flexibility and rotation of the multiple points 135 radially outwardly.

Figure 13G:
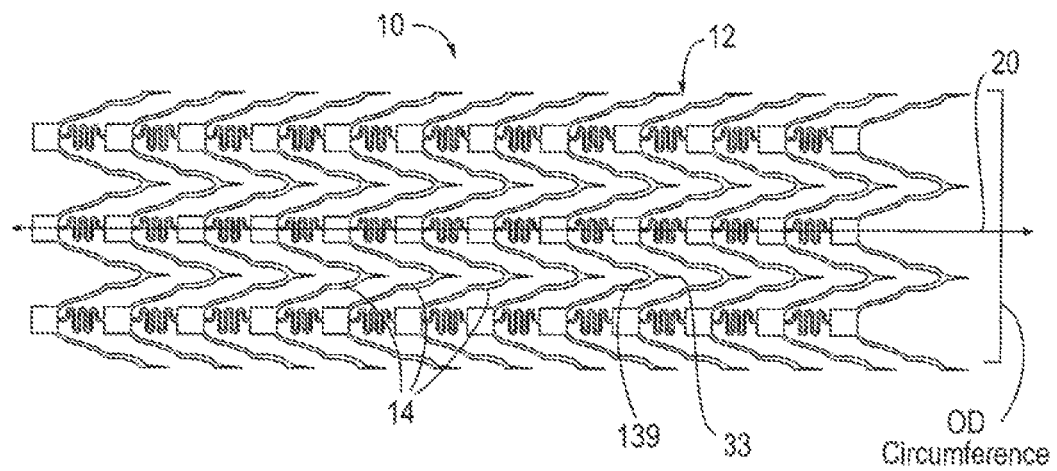
Figure 13H:
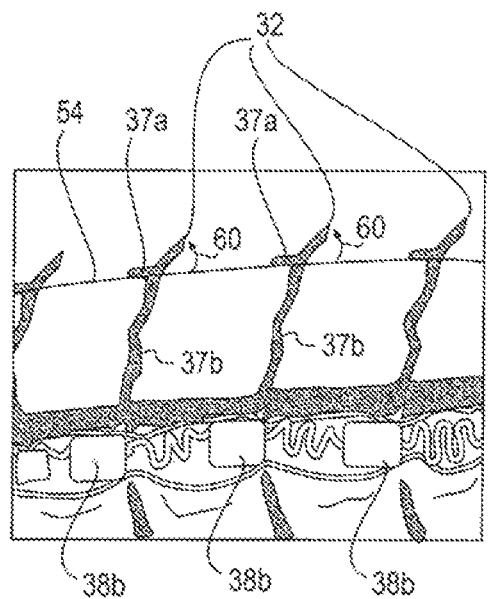
FIG. 13H illustrates the embodiment depicted in FIG. 13G having the microstructures in a deployed position.

FIG. 13G illustrates an embodiment of the expandable body 12 wherein the free ends 32 of the microstructures 14 have a single point 33 and curved inner edge 139. And, FIG. 13H illustrates the microstructures of FIG. 13G in a deployed position. FIG. 13H provides a view similar to FIG. 12C wherein circumferential movement pulls the affixed ends of the first and second supports 37a, 37b apart which moves the free end 32. Such movement of the free end 32 projects the free end 32 radially outwardly, as indicated by arrow 60. As mentioned, such projection may be due to friction created between the free end 32 and the expandable member 54 as the expandable member 54 expands the expandable body 12.

Figure 14A:
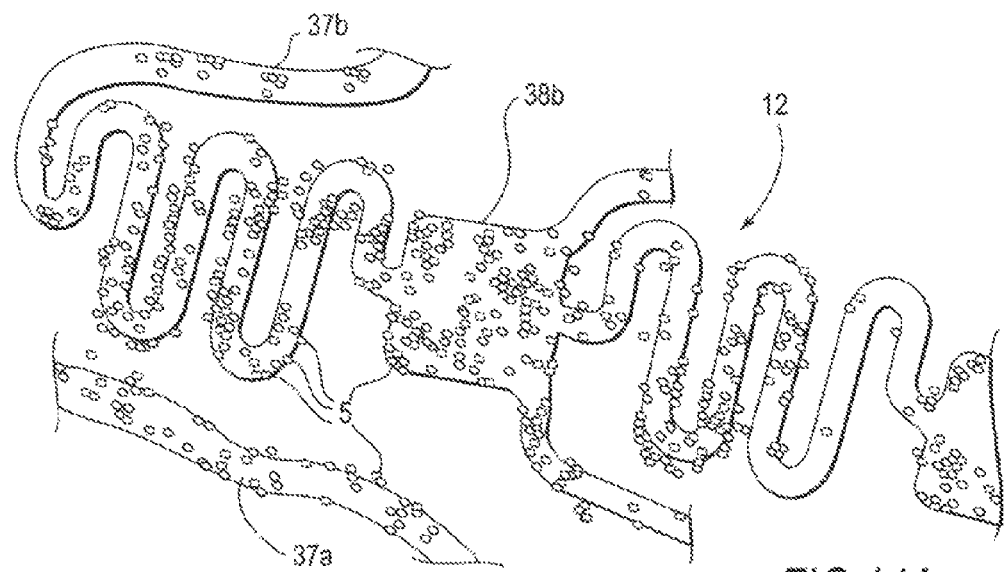
FIGS. 14A-14B illustrate an embodiment of the expandable body 12 shown in FIGS. 13G and 13H having cells 5 seeded thereon.
Figure 14B:
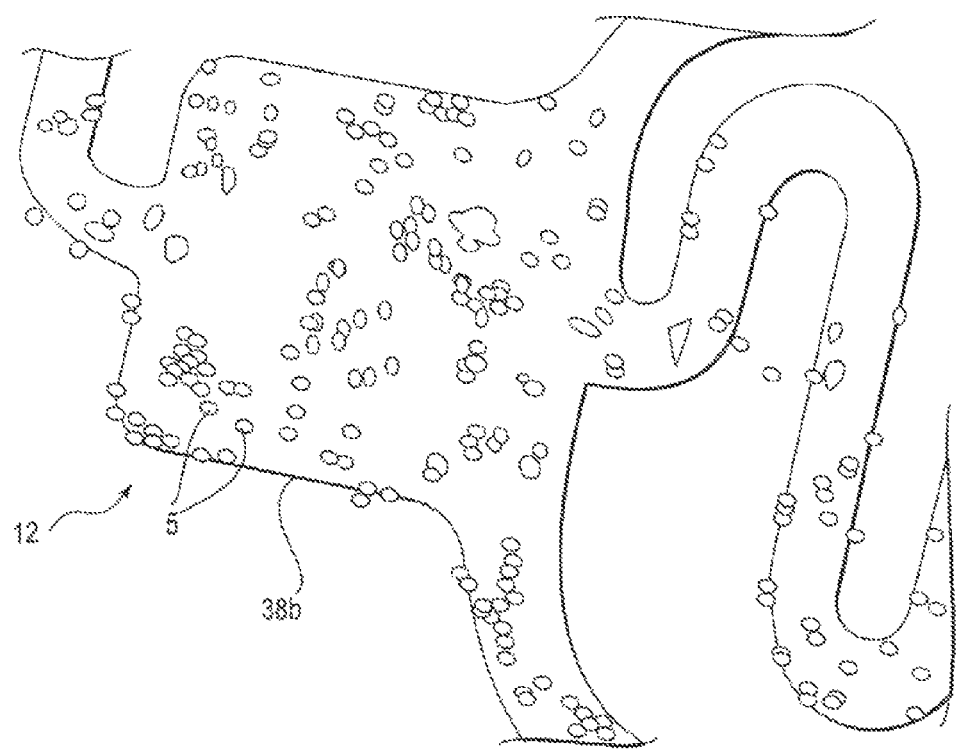

FIGS. 14A-14B illustrate an embodiment of the expandable body 12 shown in FIGS. 13G and 13H having cells 5 seeded thereon. FIG. 14A illustrates a portion of the expandable body 12 showing one of the adjacent portions 38b and first and second supports 37a, 37b of a microstructure. Cells 5 are shown covering surfaces of the expandable body 12, wherein the roundish shapes represent cell nuclei and the cytoplasms of the cells extend therebetween. FIG. 14B provides an enlarged view of a portion of the expandable body 12 shown in FIG. 14A. Here, the adjacent portion 38b of the expandable body 12 of FIG. 14A is shown enlarged and again the roundish shapes represent cell nuclei and the cytoplasms of the cells extend therebetween.

Embodiments for Repairing Aneurysms

As mentioned previously, the cell-seeded expandable bodies of the present invention may be used to anchor a tube or graft to the vessel walls surrounding an aneurysm. The cells are seeded on the expandable bodies as described above. The cells may then be delivered to the vessel walls to increase anchorage of the tube. The cells can also be delivered to the blood vessel lumen, the blood vessel walls and/or the outer surface of the blood vessel to encourage tissue regrowth or extra-cellular matrix formation. Or the cells may be delivered to the aneurysmal sac. This may allow for tissue regrowth within the sac, strengthening the tissue within the aneurysmal walls. Typically, smooth muscle cells will be used for such application.

Figure 15A:
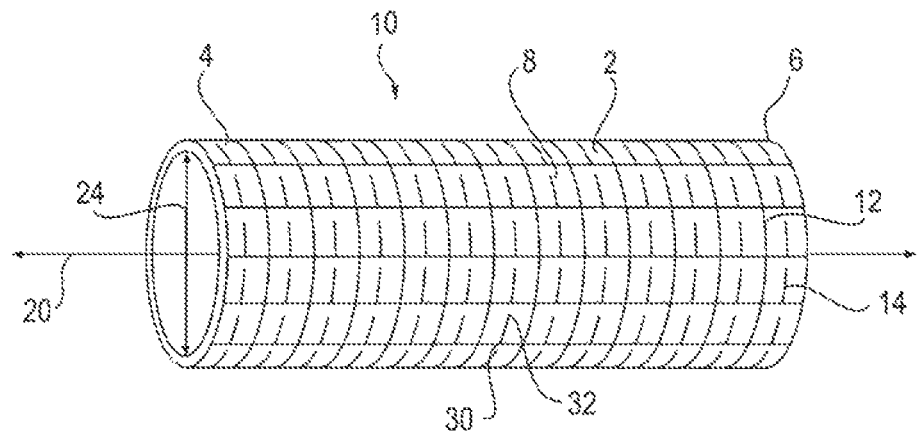
FIG. 15A illustrates an embodiment of an apparatus of the present invention in a low profile, unexpanded state wherein the microstructures are in an undeployed position.
Figure 15B:
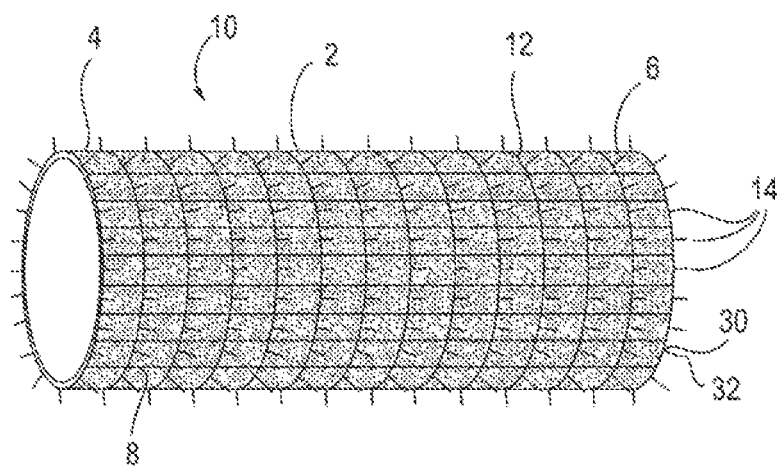
FIG. 15B illustrates the apparatus of FIG. 15A in the expanded state wherein the microstructures are in a deployed position, extending radially outwardly from the tube.

Referring to FIG. 15A, an embodiment of an apparatus 10 of the present invention for treating an aneurysm is illustrated; the apparatus 10 comprises a tube 2 having a first end 4, a second end 6 and a tube wall 8 extending between the first and second ends 4, 6. In addition, the apparatus 10 comprises an expandable body 12 attached to the tube wall 8 including at least one microstructure 14. Each microstructure 14 has an attached end 30 attached to the body and a free end 32 in an undeployed position. FIG. 15A illustrates the apparatus 10 in an unexpanded state wherein the microstructures 14 are in the undeployed position. Here, the microstructures 14 are preferably aligned or flush with an outer surface of the apparatus 10 so that the surface does not include substantial protrusions. Alternatively, the microstructures 14 may be positioned below the surface of the apparatus 10. FIG. 15A also shows cross-sectional diameter 24 and longitudinal axis 20. FIG. 15B illustrates the microstructures 14 in the deployed position wherein the free ends 32 project radially outwardly from the tube 2.

It may be appreciated that any number of microstructures 14 may be present and may be arranged in a variety of patterns along the entire length of the body 12 or along any subportion. For example, FIGS. 15A-15B illustrate an embodiment wherein the microstructures 14 are present along the entire length of the body 12 and the body 12 extends along the entire length of the tube 2. Alternatively, the microstructures 14 may be present in select locations, such as near the first end 4, near the second end 6, or near both ends 4, 6 while the body 12 extends along the entire length of the tube. These particular arrangements of microstructures 14 may be useful in anchoring the apparatus 10 across an aneurysm.

Figure 16:
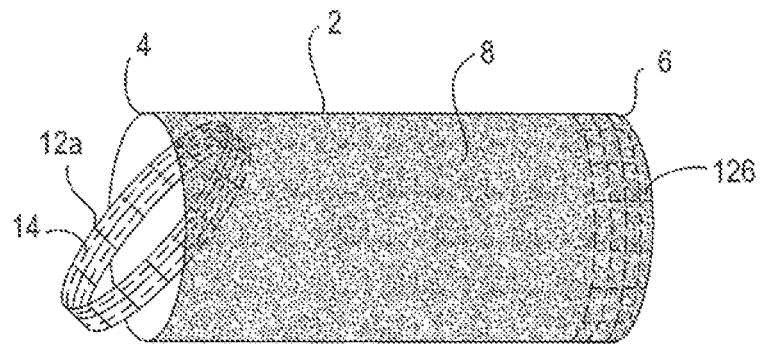
FIG. 16 depicts an embodiment including a tube and two removable expandable bodies which are sized for positioning within the tube.

Referring now to FIG. 16, an embodiment of a system of the present invention is provided including a tube 2 having a first end 4, a second end 6 and a tube wall 8 extending between the first and second ends 4, 6, and at least one expandable body 12 which is sized for positioning within the tube 2. Here, two expandable bodies 12a, 12b are shown, a first expandable body 12a partially in place near the first end 4 to illustrate its movability and a second expandable body 12b in place near the second end 6. Thus, the at least one expandable body 12 may be positioned at any location along the length of the tube 2, including extending beyond the ends 4, 6 of the tube.

Figure 17:
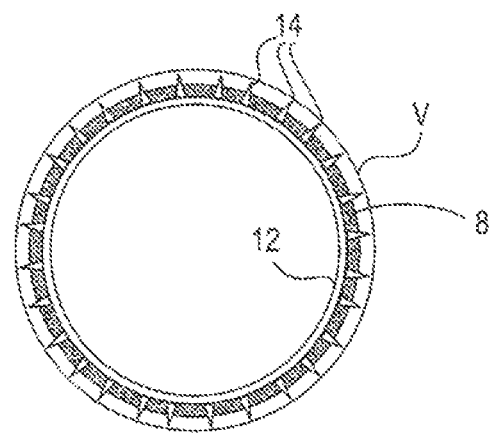
FIG. 17 is a cross-sectional view of the embodiment of FIG. 16 illustrating the penetration of the microstructures through the tube and into the surrounding vessel wall.

When the expandable body 12 is positioned within the tube 2, expansion of the body 12 and deployment of the microstructures 14 occurs within the tube 2 so that further expansion penetrates the microstructures 14 through the tube wall 8, as illustrated in FIG. 17. FIG. 17 provides a cross-sectional view of the expandable body 12 within a tube 2 and illustrates a plurality of microstructures 14 penetrating the tube wall 8. FIG. 17 also illustrates the microstructures 14 further penetrating a surrounding blood vessel wall V. Thus, the microstructures 14 may be used to anchor the apparatus 10 within the blood vessel and to deliver cells to the blood vessel in a manner similar to that in which the expandable body 12 is used alone.

Figure 18:
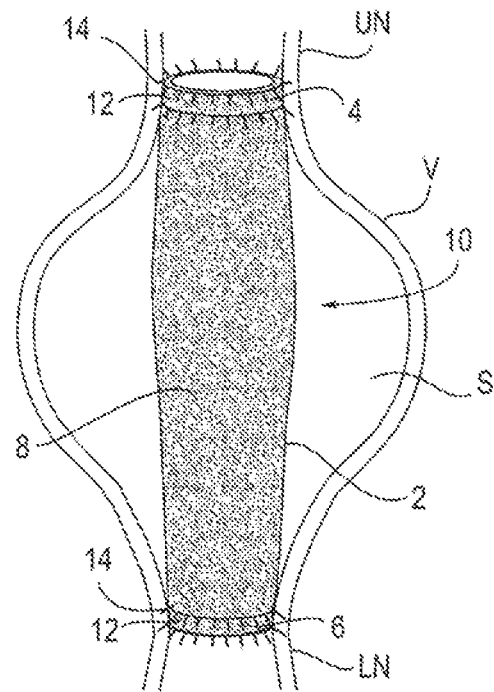
FIG. 18 illustrates an aneurysm within a blood vessel and an apparatus of the present invention positioned across the aneurysmal sac.
Figure 19:
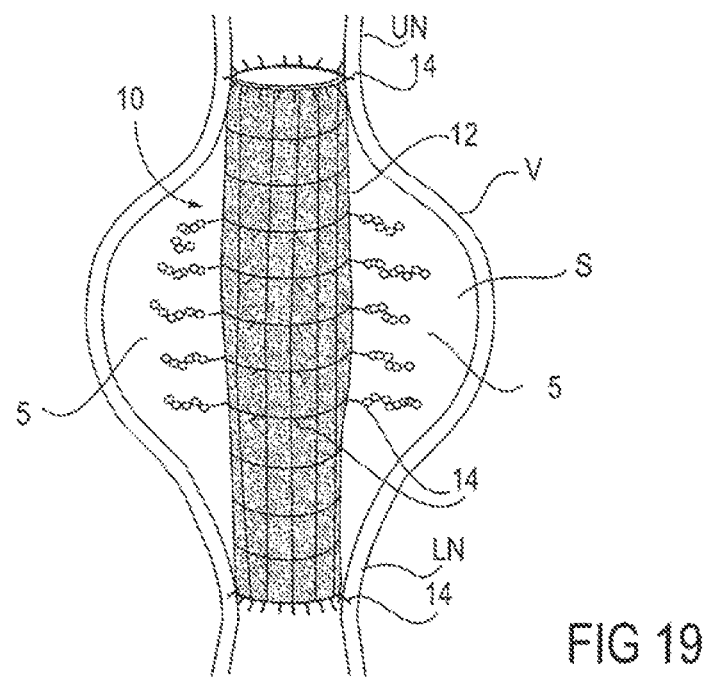
FIG. 19 illustrates an apparatus of the present invention positioned across the aneurysmal sac and the delivery of cells to this sac through microstructures.

FIG. 18 illustrates an aneurysm within a blood vessel V. An aneurysm comprises a sac S caused by abnormal dilation of the wall of the blood vessel V and may occur within any blood vessel in the body. Life-threatening aneurysms can occur in cerebral blood vessels and the aorta, to name a few. Repair of such aneurysms typically involves bridging the sac S with a graft material, wherein the graft is at least secured to the upper neck UN and lower neck LN of the blood vessel V near the ends of the sac S. This provides a conduit for blood flow through the blood vessel V, preventing further collection of blood in the aneurysmal sac S and reducing the progression of growth of the aneurysm and the risk of sac rupture due to blood pressure. In addition, the microstructures 14 can also be used to deliver cells 5. Cells 5, such as unmodified smooth muscle cells may be delivered into the vessel wall or deposited on the inner or outer surfaces of the vessel wall to enhance sealing by cell proliferation and production of extracellular matrix components. These cells 5 may also be delivered to the aneurysmal sac S, as illustrated in FIG. 19. In this embodiment, the expandable body 12 extends the length of the tube wall 8 and has microstructures 14 near the first end 4 and second end 6 to anchor the apparatus 10 in place and has microstructures 14 between the ends 4, 6 for delivery of cells 5 to the aneurysmal sac S.

The present invention may be particularly suitable for repair of abdominal aortic aneurysms. An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries at a bifurcation.

Figure 20:
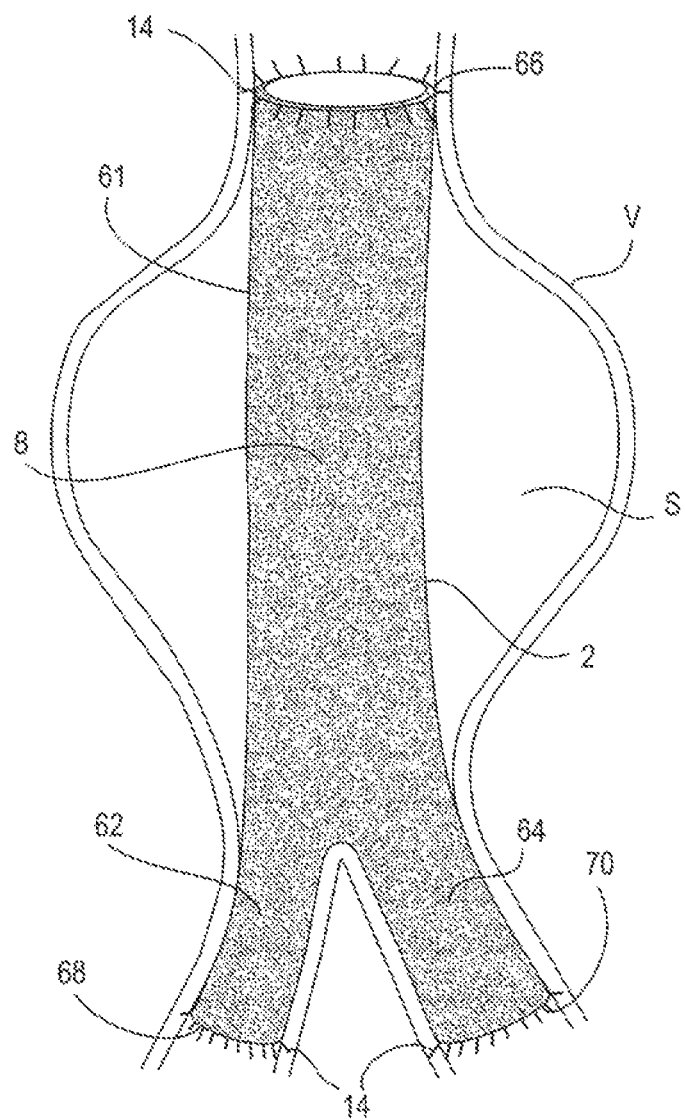
FIG. 20 illustrates the embodiment of a bifurcated apparatus of the present invention positioned within an abdominal aortic aneurysm.

To treat abdominal aortic aneurysms, the apparatus 10 is shaped to be disposed at least partially within the aneurysm. In particular, the tube 2 is shaped to fit the aortic geometry. For example, FIG. 20 illustrates an embodiment of the apparatus 10 of the present invention shaped to fit within the abdominal aorta, traversing the bifurcation. Thus, the tube 2 includes a main shaft 61, a first leg 62, and a second leg 64. This embodiment further includes three expandable bodies, a first expandable body 66 disposed near the end of the main shaft 61, a second expandable body 68 disposed near the end of the first leg 62 and a third expandable body 70 disposed near the end of the second leg 64, as shown. Positioning of these expandable bodies 66, 68, 70 are intended to provide anchoring for the apparatus within the aorta and iliac arteries surrounding the abdominal aortic aneurysm. Alternatively, one or more expandable bodies may extend over larger portions of the tube wall 8, including over the entire tube 2. Again, the microstructures 14 provide delivery of cells 5 to the blood vessel V, areas within or surrounding the blood vessel, and/or within the aneurysmal sac S.

Delivery of Cells from Expandable Body

Positioning of the apparatus of the present invention is typically performed via standard catheterization techniques. These methods are well known to cardiac physicians and are described in detail in many standard references. Examples of such positioning will be provided in relation to the vascular system, however, such example is not intended to limit the scope of the invention. In brief, percutaneous access of the femoral or brachial arteries is obtained with standard needles, guide wires, sheaths, and catheters. After engagement of the coronary arteries with a hollow guiding catheter, a wire is passed across the coronary stenosis where the apparatus is to be deployed. The apparatus is then passed over this wire, using standard coronary interventional techniques, to the site where therapy is to be delivered.

Figure 21:
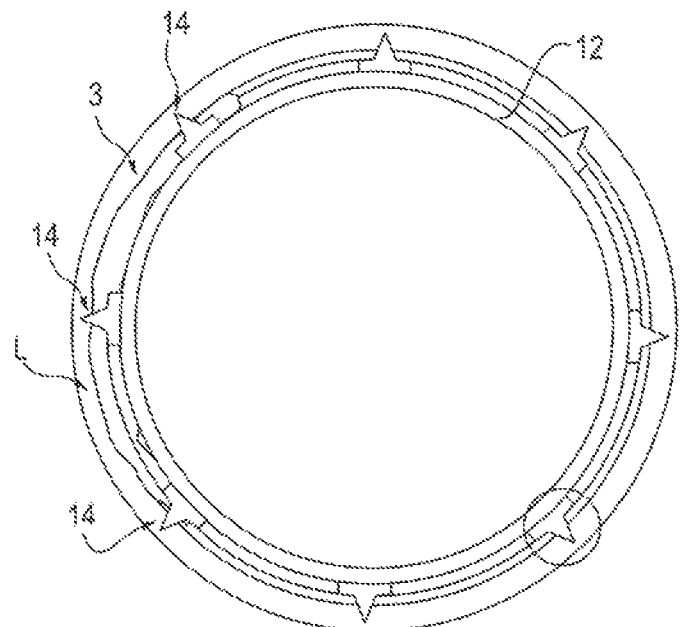
FIG. 21 illustrates a cross-sectional view of the expandable body expanded inside a blood vessel lumen, and FIG. 21A provides an exploded view of a microstructure penetrating the wall of the vessel lumen.
Figure 21A:
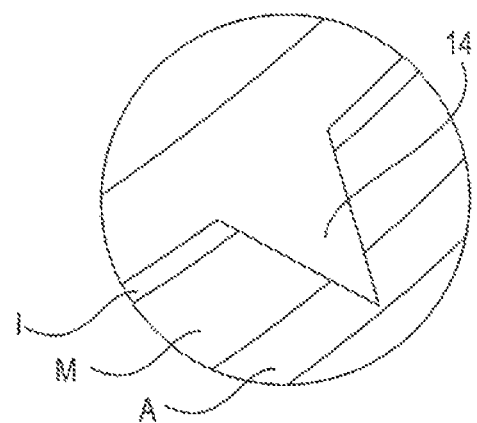

The apparatus is then delivered and expanded to force the microstructures 14 through the tissue so the microstructure tips reach within the vessel wall, as shown in FIGS. 21-21A. FIG. 21 shows a cross-sectional view of the expandable body 12 expanded inside a blood vessel lumen L. Microstructures 14 pierce through a layer of compressed plaque 3 and into the wall of the lumen L. FIG. 21A provides an exploded view of a microstructure 14 penetrating the wall of the lumen L. Here, an intimal layer I, medial layer M and adventitial layer A are shown. The microstructure 14 may penetrate any or all of the layers I, M, A, including penetrating through the wall of the lumen L to the peri-adventitial space. FIG. 21A illustrates penetration to the adventitial layer A. Such penetration provides controlled dissection of the vessel wall by the microstructures and provides pathways for migration of the cells into the blood vessel wall, and, when desired, into the adventitial layer A. Cells seeded on the surfaces of the expandable body migrate from the expandable body to the surrounding tissue environment. In some cases it may be desired to penetrate the microstructures through to the peri-adventitial space. The cells which are held within the microstructures then enter the lumen wall or are deposited peri-vascularly where they perform their desired biological function. If the apparatus is intended to function in a stent-like manner, the apparatus is then left behind in its expanded state.

Applications

As mentioned previously, the present invention may be utilized for any sort of treatment which involves delivery of a therapeutic agent and/or anchoring of a device. The devices could be introduced into various body lumens, such as those found in the vascular system, the pulmonary system, the gastro-intestinal tract, the urinary tract and the reproductive tract, to name a few. The function of the microstructures includes but is not limited to facilitating delivery of a therapeutic agent, such as cells, securing the device in place and providing a mechanical seal to the lumen wall.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A system for treating a patient comprising:
   a tube having a first end, a second end and a tube wall extending between the first and second ends;
   an expandable body attached to the tube wall having a proximal end, a distal end, a longitudinal axis therebetween, and at least one microstructure having an attached end attached to the body and a free end which is projectable radially outwardly from the expandable body; and
   a plurality of cells disposed on at least one surface of the expandable body;
   wherein:
   the surface provides controlled time dependent release of a substance over time;
   at least some of the plurality of cells have been genetically engineered to express a therapeutic gene; and
   the substance comprises an agent that controls the activity of the therapeutic gene contained with the cells.

2. A system as in claim 1, wherein the at least one surface is located on an outer surface of the expandable body.

3. A system as in claim 2, wherein the surface comprises a nanoporous metallic coating wherein the coating has a morphology that provides controlled time dependent release of a substance over time.

4. A system as in claim 3, wherein the substance promotes cell adherence and/or cell growth.

5. A system as in claim 4, wherein the substance comprises a member of the $TGF_\beta$ family.

6. A system as in claim 5, wherein the substance comprises $TGF_{\beta 1}$.

7. A system as in claim 3, wherein the substance augments growth of endothelial cells and/or smooth muscle cells.

8. A system as in claim 7, wherein the substance comprises VEGF, bFGF, PLGF, PDGF, or a combination of these.

9. A system as in claim 1, wherein the surface includes pores.

10. A system as in claim 9, wherein the pores are sized to allow positioning of the cells within the pores.

11. A system as in claim 1, further comprising a substance on the surface which improves adhesion of the plurality of cells to the surface.

12. A system as in claim 11, wherein the substance comprises polymer substrates, biocompatible proteins, growth factors, extracellular matrix components or a combination of any of these.

13. A system as in claim 1, wherein the at least one surface is located on an internal lumen within the at least one microstructure.

14. A system as in claim 13, wherein the plurality of cells comprise cells which are non-autologous to the patient, and wherein the non-autologous cells are disposed within the at least one microstructure so that the non-autologous cells are immunologically isolated from the patient's immune system.

15. A system as in claim 1, wherein expansion of the body creates forces which deploy the at least one microstructure from an undeployed position wherein the free end is substantially aligned with an outer surface of the expandable body to a deployed position wherein the free end projects radially outwardly from the expandable body.

16. A system as in claim 1, wherein the plurality of cells comprise smooth muscle cells, autologous smooth muscle cells, non-autologous smooth muscle cells, stem cell derived smooth muscle cells, or smooth muscle progenitor cells.

17. A system as in claim 1, wherein the plurality of cells comprise endothelial cells.

18. A system as in claim 1, wherein the plurality of cells comprise epithelial cells.

19. A system as in claim 1, wherein the plurality of cells comprise stem cell derived cell populations.

20. A system as in claim 1, wherein the plurality of cells comprise embryonic stem cells and/or derivatives of embryonic stem cells.

21. A system as in claim 1, wherein the plurality of cells comprise pancreatic beta cells, myofibroblasts, cardiac myocytes, skeletal muscle satellite cells, dendritic cells, multi-potential somatic stem cells, derivatives of multi-potential somatic stem cells, neuronal cells, glial cells, hepatocytes, or endocrine cells.

22. A system as in claim 1, wherein the plurality of cells are genetically modified.

23. A system as in claim 22, wherein the plurality of cells are genetically modified to over-express endothelial nitric oxide synthase, inducible nitric oxide synthase, $TGF_{\beta 1}$, IL-4, IL-10, IL-13, PDGF, PLGF, VEGF, or a combination of these.

24. A system as in claim 1, wherein the expandable body is sized for positioning within a body lumen having a wall.

25. A system as in claim 24, wherein the free end is projectable radially outwardly from the expandable body a distance sufficient to penetrate the wall of the body lumen.

26. A system as in claim 24, wherein the body lumen comprises a blood vessel.

27. A system as in claim 24, wherein the body lumen is disposed within the gastro-intestinal tract, the pulmonary system, the urinary system or the reproductive system.

28. A system as in claim 1, for repair of an aneurysm in a blood vessel of a patient.

29. A system as in claim 28, wherein the blood vessel comprises a segment of an aorta having two iliac arteries therewith at an aortic bifurcation, and wherein the tube further comprises an opening between the first end and the second end to align with one of the iliac arteries.

* * * * *